(12) United States Patent
Griffin et al.

(10) Patent No.: US 11,826,097 B2
(45) Date of Patent: Nov. 28, 2023

(54) FORMING RADIAL EMISSIONS FROM OPTICAL FIBERS

(71) Applicant: Cyclone Biosciences, LLC, Phoenix, AZ (US)

(72) Inventors: Stephen E. Griffin, Peoria, AZ (US); Stuart F Watson, Mesa, AZ (US)

(73) Assignee: CYCLONE BIOSCIENCES, LLC, Tucson, AZ (US)

( * ) Notice: Subject to any disclaimer, the term of this patent is extended or adjusted under 35 U.S.C. 154(b) by 364 days.

(21) Appl. No.: 17/224,354

(22) Filed: Apr. 7, 2021

(65) Prior Publication Data

US 2021/0330383 A1 Oct. 28, 2021

Related U.S. Application Data

(60) Continuation-in-part of application No. 16/122,982, filed on Sep. 6, 2018, now Pat. No. 10,993,768, which
(Continued)

(51) Int. Cl.
*G02B 6/26* (2006.01)
*G02B 6/42* (2006.01)
(Continued)

(52) U.S. Cl.
CPC ............ *A61B 18/22* (2013.01); *A61N 5/0601* (2013.01); *A61N 5/062* (2013.01); *G02B 6/0003* (2013.01); *A61B 2018/00404* (2013.01); *A61B 2018/00577* (2013.01); *A61B 2018/2222* (2013.01); *A61B 2018/2244* (2013.01);
(Continued)

(58) Field of Classification Search
CPC .......... G02B 6/32; G02B 6/262; G02B 6/005; G02B 6/0028; G02B 6/003; G02B 6/0033; A61B 18/22; A61B 2018/2272; A61B 18/24; A61B 18/201; A61B 18/202;
(Continued)

(56) References Cited

U.S. PATENT DOCUMENTS

| 4,669,467 A | 6/1987 | Willett |
| 4,672,961 A | 6/1987 | Davies |

(Continued)

*Primary Examiner* — Kaveh C Kianni
*Assistant Examiner* — Hung Q Lam
(74) *Attorney, Agent, or Firm* — Quarles & Brady LLP; Yakov S. Sidorin

(57) ABSTRACT

Articles of manufacture, including terminations of or attachments to optical fibers are configured to substantially prevent axial emission and redirect radially most if not all light emanating from optical fibers. In that, a termination may include a fiber cap of a unitary construction of a tube and an optical element disposed to face a sealed end of the tube and dividing a hollow of the tube and having a conical surface, or an optical element dividing the hollow and complemented by a cone. An example of termination includes an optical fiber element having an up-tapered end with a maximum taper-diameter exceeding the core-diameter and ending at a conical element with an apex angle from about 70° to about 100°. Articles of manufacture additionally including mounting contraptions cooperating such terminations with cannulae to form an attachment to a laser system. Methods for transmitting light through such articles of manufacture.

18 Claims, 14 Drawing Sheets

FIG. 16A

Related U.S. Application Data is a division of application No. 14/944,266, filed on Nov. 18, 2015, now Pat. No. 10,092,356.

(51) Int. Cl.

| | | |
|---|---|---|
| *G02B 6/32* | (2006.01) | |
| *G02B 6/34* | (2006.01) | |
| *G02B 6/36* | (2006.01) | |
| *G02B 6/38* | (2006.01) | |
| *A61B 18/22* | (2006.01) | |
| *F21V 8/00* | (2006.01) | |
| *A61N 5/06* | (2006.01) | |
| *A61B 18/00* | (2006.01) | |
| *A61N 5/067* | (2006.01) | |

(52) U.S. Cl.
CPC ........... *A61B 2018/2261* (2013.01); *A61B 2018/2266* (2013.01); *A61B 2018/2272* (2013.01); *A61N 5/067* (2021.08); *A61N 2005/063* (2013.01); *G02B 6/262* (2013.01)

(58) Field of Classification Search
CPC .... A61B 2018/2255; A61B 2018/2266; A61B 2018/2277; A61B 5/6852
USPC ......... 385/29, 31, 33, 36, 38, 68, 74, 79, 84
See application file for complete search history.

(56) References Cited

U.S. PATENT DOCUMENTS

| | | |
|---|---|---|
| 4,718,417 A | 1/1988 | Kittrell |
| 4,732,448 A | 3/1988 | Goldenberg |
| 4,740,047 A | 4/1988 | Abe |
| 4,842,390 A | 6/1989 | Sottini |
| 4,967,745 A | 11/1990 | Hayes |
| 5,001,737 A | 3/1991 | Lewis |
| 5,019,075 A | 5/1991 | Spears |
| 5,061,265 A | 10/1991 | Abela |
| 5,074,632 A | 12/1991 | Potter |
| 5,093,877 A | 3/1992 | Aita |
| 5,104,392 A | 4/1992 | Kittrell |
| 5,106,387 A | 4/1992 | Kittrell |
| 5,125,404 A | 6/1992 | Kittrell |
| 5,192,278 A | 3/1993 | Hayes |
| 5,199,431 A | 4/1993 | Kittrell |
| 5,231,684 A | 7/1993 | Narciso |
| 5,242,438 A | 9/1993 | Saadatmanesh et al. |
| 5,269,777 A | 12/1993 | Doiron |
| 5,290,275 A | 3/1994 | Kittrell |
| 5,292,320 A | 3/1994 | Brown |
| 5,342,355 A | 8/1994 | Long |
| 5,343,543 A | 8/1994 | Novak, Jr. |
| 5,354,294 A | 10/1994 | Chou |
| 5,428,699 A | 6/1995 | Pon |
| 5,468,239 A | 11/1995 | Tanner |
| 5,486,171 A | 1/1996 | Chou |
| 5,495,541 A | 2/1996 | Murray |
| 5,496,307 A | 3/1996 | Daikuzono |
| 5,496,308 A | 3/1996 | Brown |
| 5,498,260 A | 3/1996 | Rink |
| 5,509,917 A | 4/1996 | Cecchetti et al. |
| 5,512,078 A | 4/1996 | Griffin |
| 5,530,780 A | 6/1996 | Ohsawa |
| 5,537,499 A | 7/1996 | Brekke |
| 5,562,657 A | 10/1996 | Griffin |
| 5,571,099 A | 11/1996 | Purcell |
| 5,695,583 A | 12/1997 | Van Den Bergh |
| 5,737,472 A | 4/1998 | Bernasson et al. |
| 5,807,390 A | 9/1998 | Fuller |
| 5,824,005 A | 10/1998 | Motamedi |
| 5,908,415 A | 6/1999 | Sinofsky |
| 6,102,905 A | 8/2000 | Baxter |
| 6,113,589 A | 9/2000 | Levy |
| 6,246,817 B1 | 6/2001 | Griffin |
| 6,270,492 B1 | 8/2001 | Sinofsky |
| 6,284,085 B1 | 9/2001 | Gwo |
| 6,398,777 B1 | 6/2002 | Navarro |
| 6,398,778 B1 | 6/2002 | Gu |
| 6,522,806 B1 | 2/2003 | James |
| 6,687,436 B2 | 2/2004 | Griffin |
| 6,712,526 B1 | 3/2004 | Fleenor |
| 6,818,892 B1 * | 11/2004 | Etienne ............... G01J 5/34 250/338.3 |
| 6,829,411 B2 | 12/2004 | Easley |
| 6,893,432 B2 | 5/2005 | Intintoli |
| 6,986,764 B2 | 1/2006 | Davenport |
| 7,270,656 B2 | 9/2007 | Gowda |
| 7,273,478 B2 | 9/2007 | Appling |
| 7,386,203 B2 | 6/2008 | Maitland |
| 7,463,801 B2 | 12/2008 | Brekke |
| 7,524,316 B2 | 4/2009 | Hennings |
| 7,559,329 B2 | 7/2009 | Appling et al. |
| 7,909,817 B2 | 3/2011 | Griffin |
| 8,073,297 B2 | 12/2011 | Griffin |
| 8,211,095 B2 | 7/2012 | Gowda |
| 8,257,347 B2 | 9/2012 | Neuberger |
| 8,285,097 B2 | 10/2012 | Griffin |
| 8,435,235 B2 | 5/2013 | Stevens |
| 8,851,080 B2 | 10/2014 | Gowda |
| 9,323,005 B1 | 4/2016 | Griffin |
| 9,421,065 B2 | 8/2016 | Splinter |
| 9,488,782 B2 | 11/2016 | Griffin |
| 9,618,700 B1 * | 4/2017 | Griffin ............... G02B 6/32 |
| 2002/0021869 A1 | 2/2002 | Griffin |
| 2005/0015123 A1 | 1/2005 | Paithankar |
| 2005/0165279 A1 | 7/2005 | Adler |
| 2006/0104593 A1 | 5/2006 | Gowda |
| 2006/0282068 A1 | 12/2006 | Griffin |
| 2006/0291061 A1 | 12/2006 | Iyama |
| 2007/0106286 A1 | 5/2007 | Harschack et al. |
| 2008/0287936 A1 | 11/2008 | Stinson |
| 2009/0240242 A1 | 9/2009 | Neuberger |
| 2010/0135617 A1 | 6/2010 | Novak |
| 2010/0179525 A1 | 7/2010 | Neuberger |
| 2011/0002584 A1 | 1/2011 | Griffin |
| 2011/0038580 A1 | 2/2011 | Griffin |
| 2011/0282330 A1 | 11/2011 | Harschack |
| 2011/0301584 A1 | 12/2011 | Beck |
| 2015/0057648 A1 | 2/2015 | Swift |

* cited by examiner

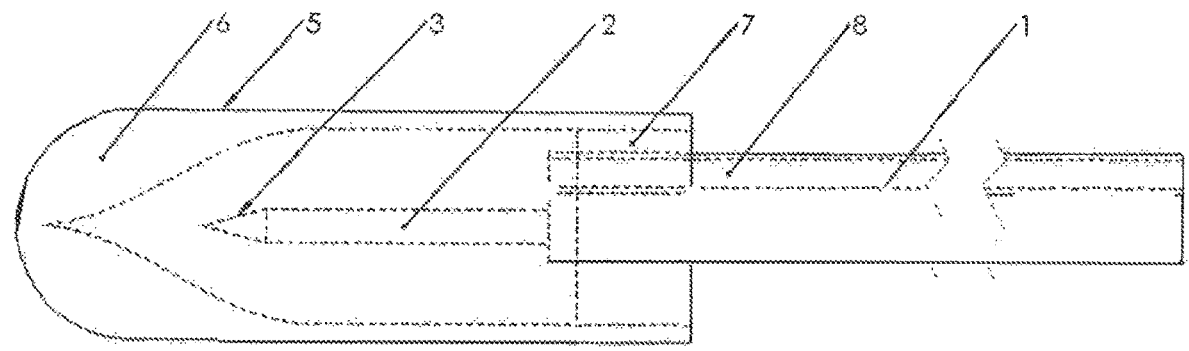
FIG. 1 (Prior Art, '390)
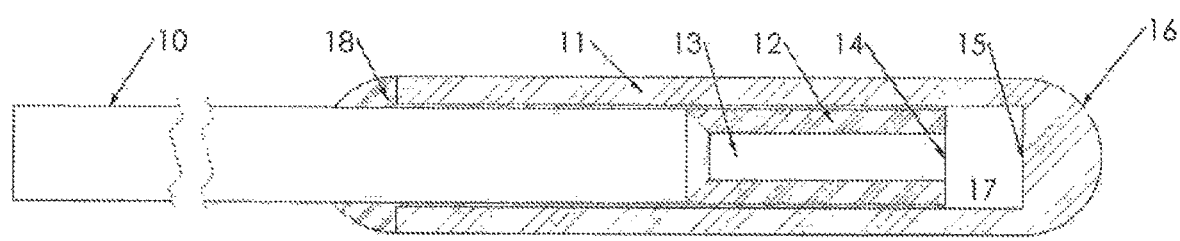
FIG. 2 (Prior Art, '877)
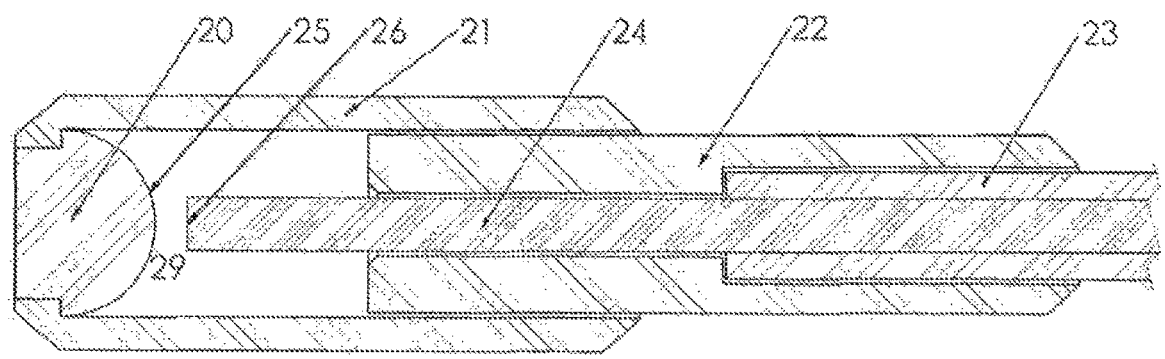
FIG. 3 (Prior Art, '684)

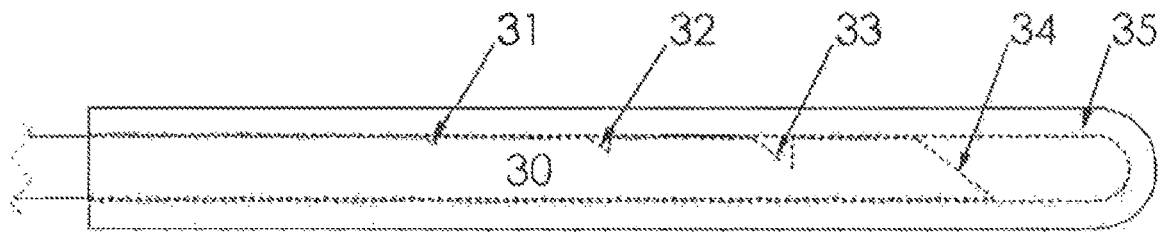
FIG. 4 (Prior Art, '320)
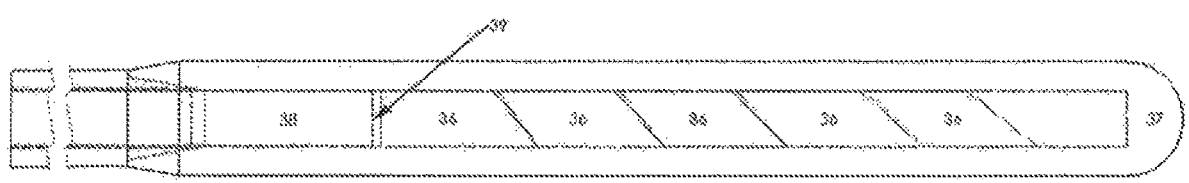
FIG. 5 (Prior Art, unpublished)
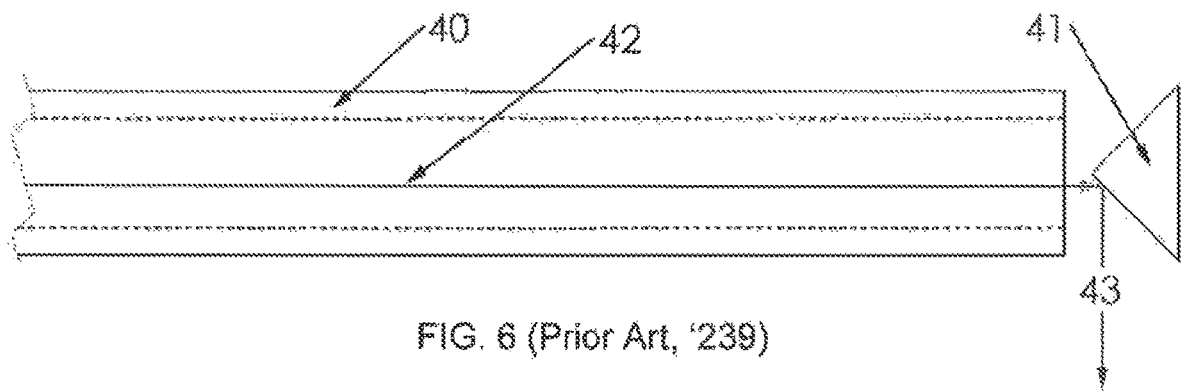
FIG. 6 (Prior Art, '239)

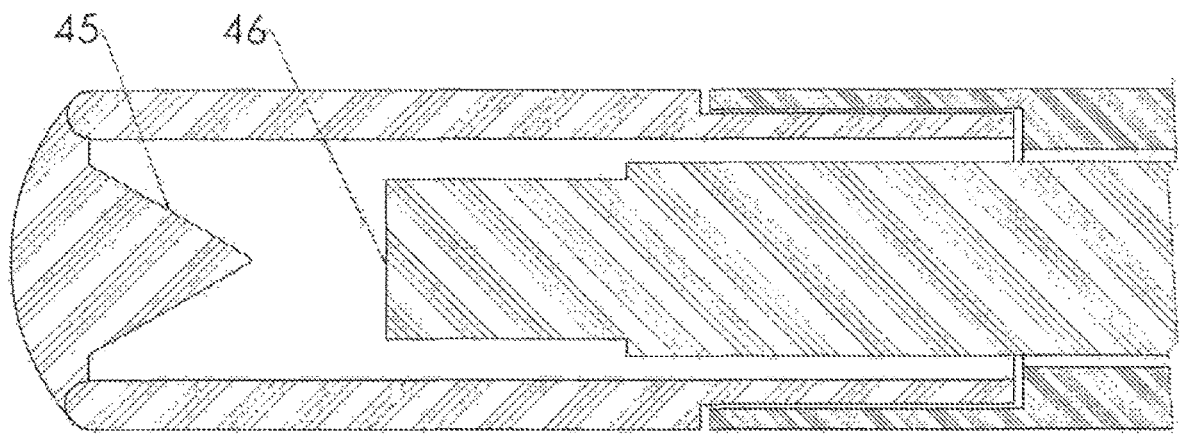
FIG. 7 (Prior Art, '235)
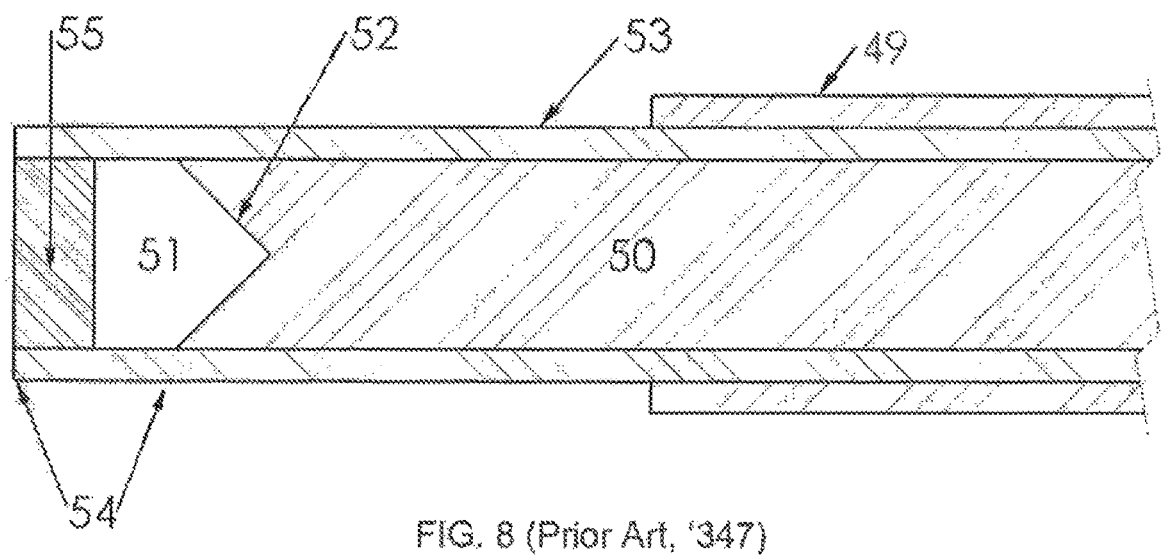
FIG. 8 (Prior Art, '347)

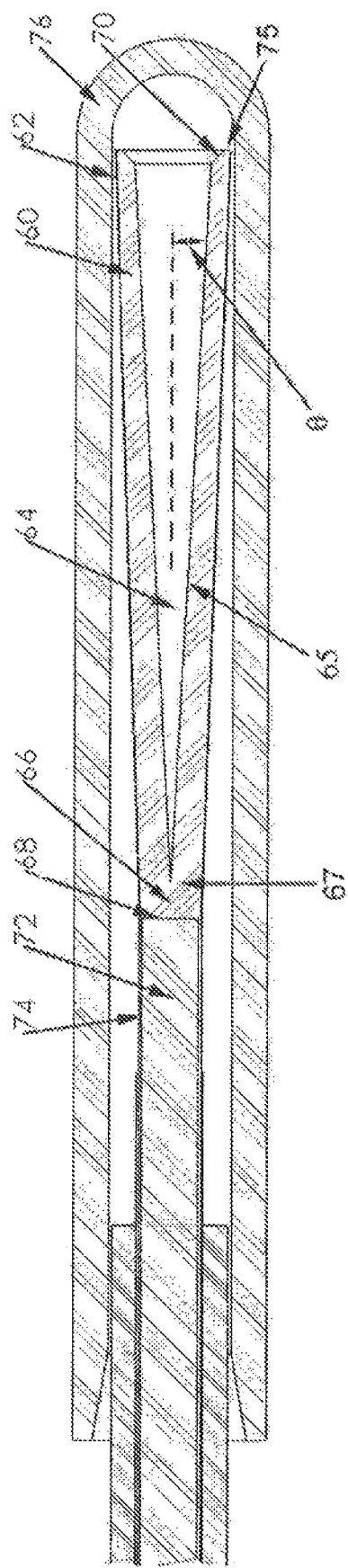
FIG. 9 (Prior Art '097)

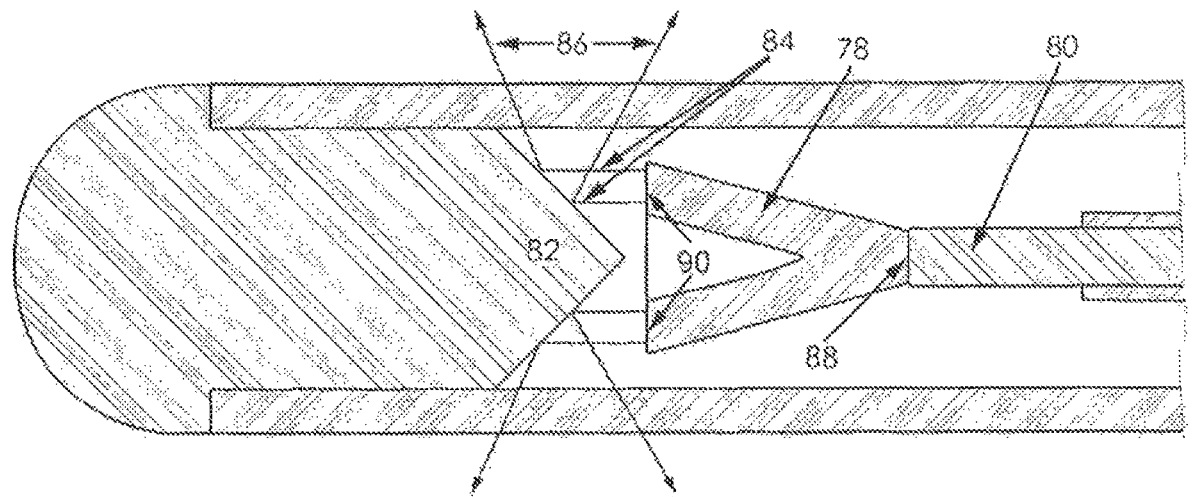
FIG. 10 (Prior Art, '438)
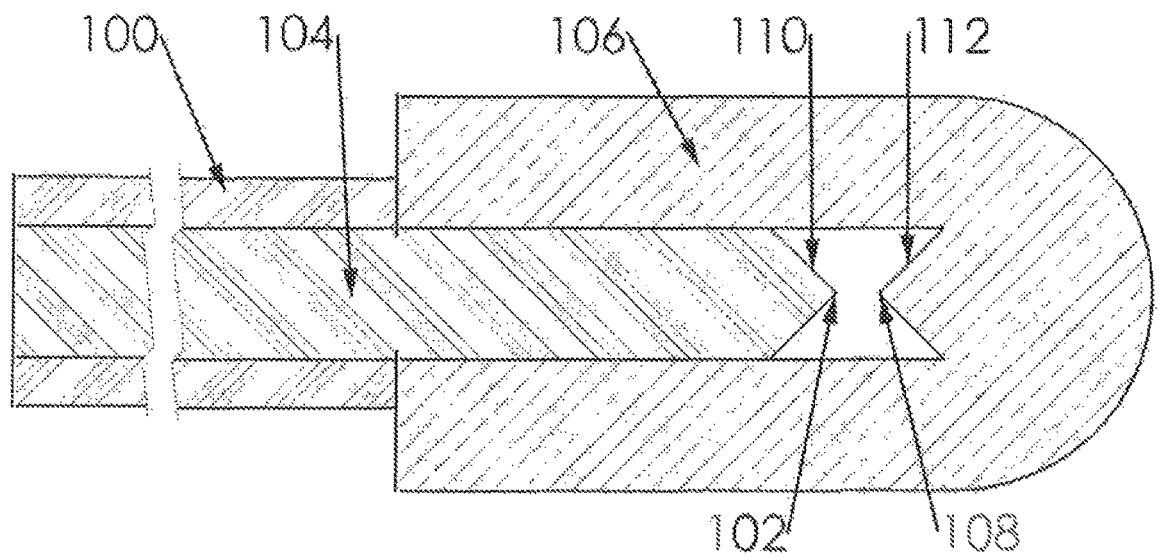
FIG. 11 (Prior Art, '242)

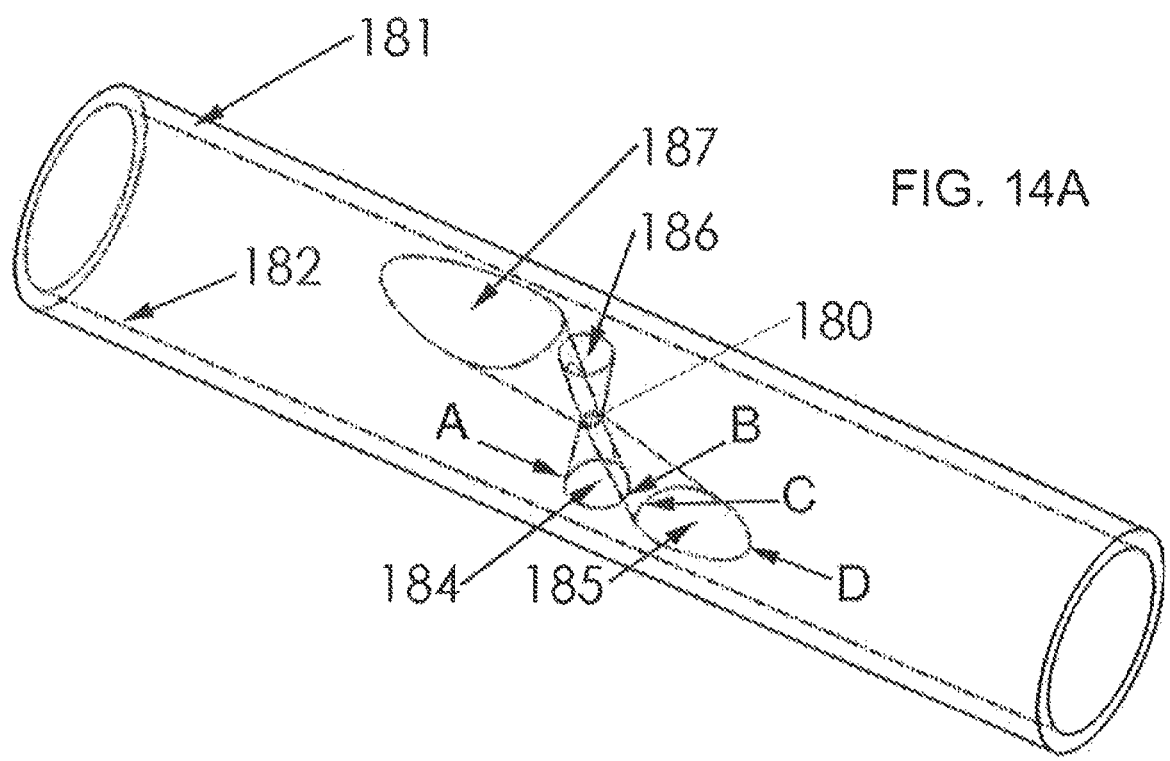
FIG. 14A
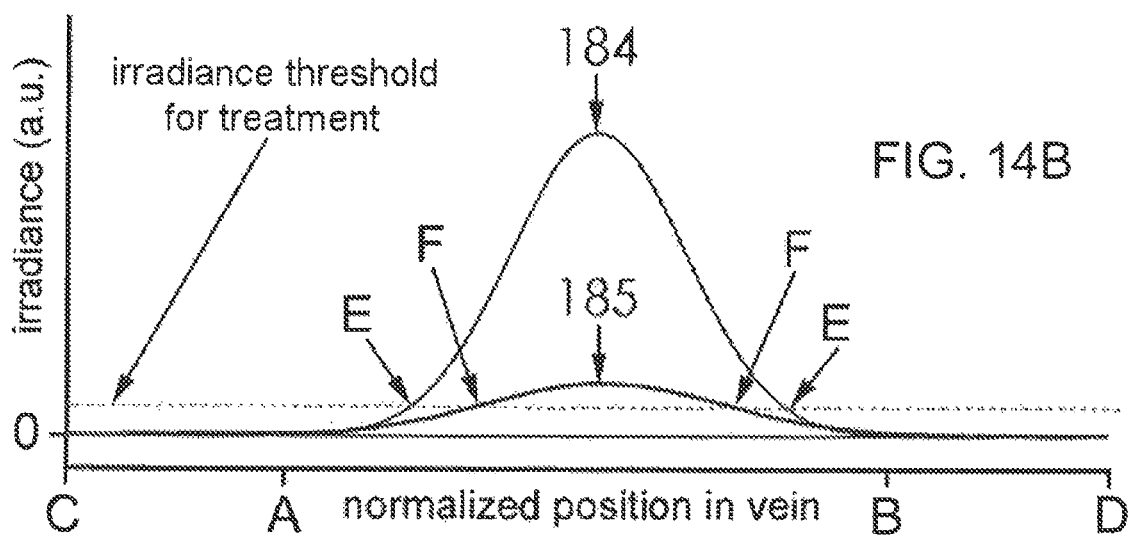
FIG. 14B
FIG. 14

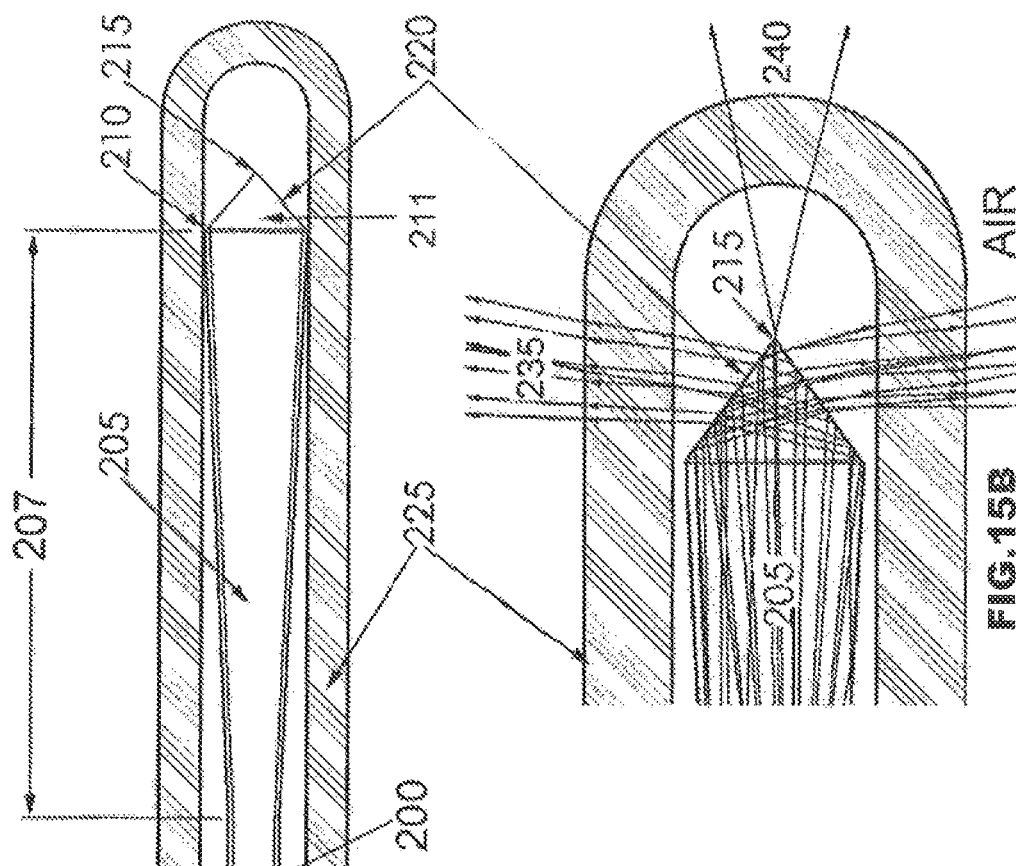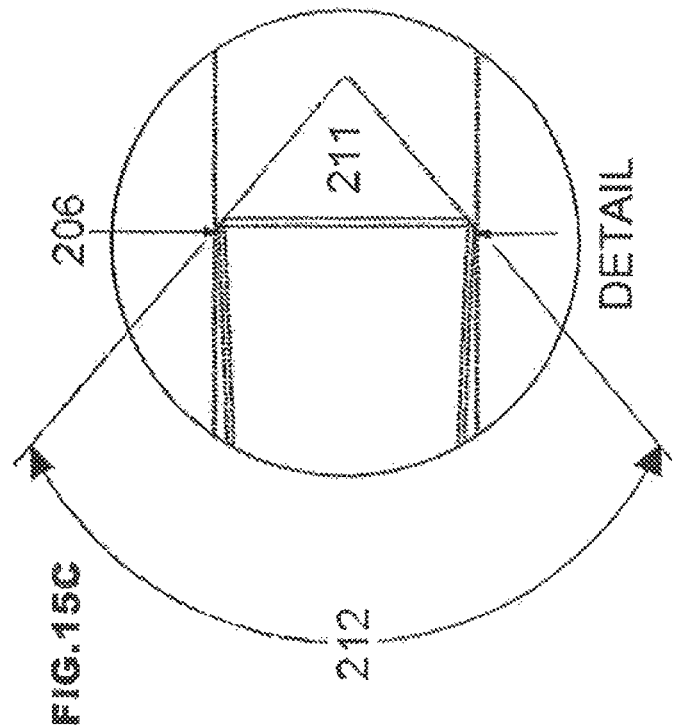
FIG. 15

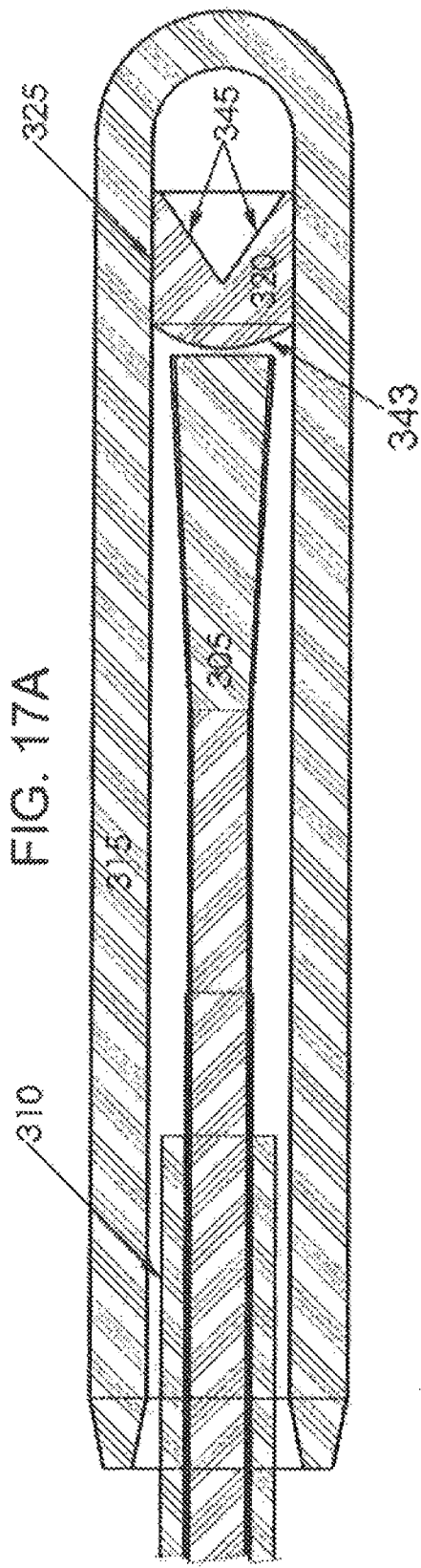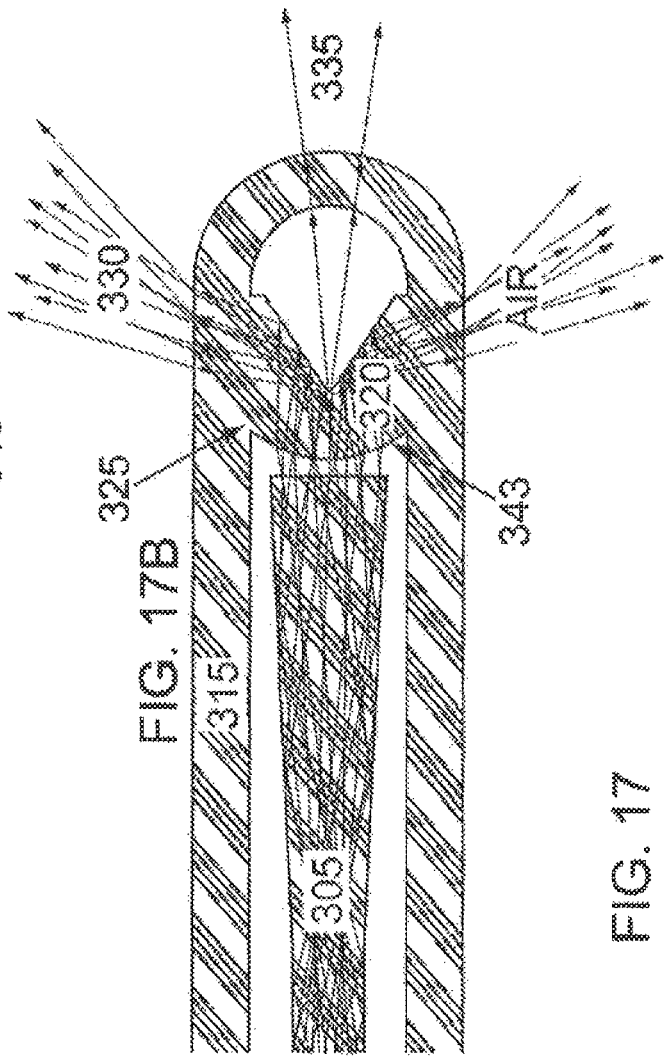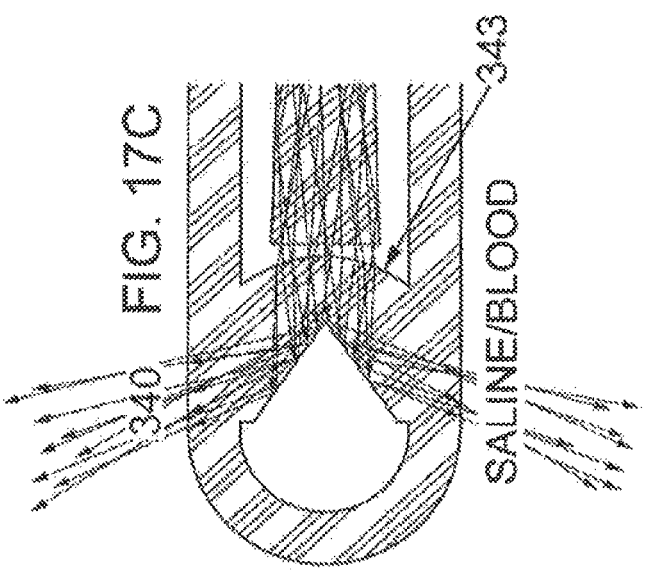

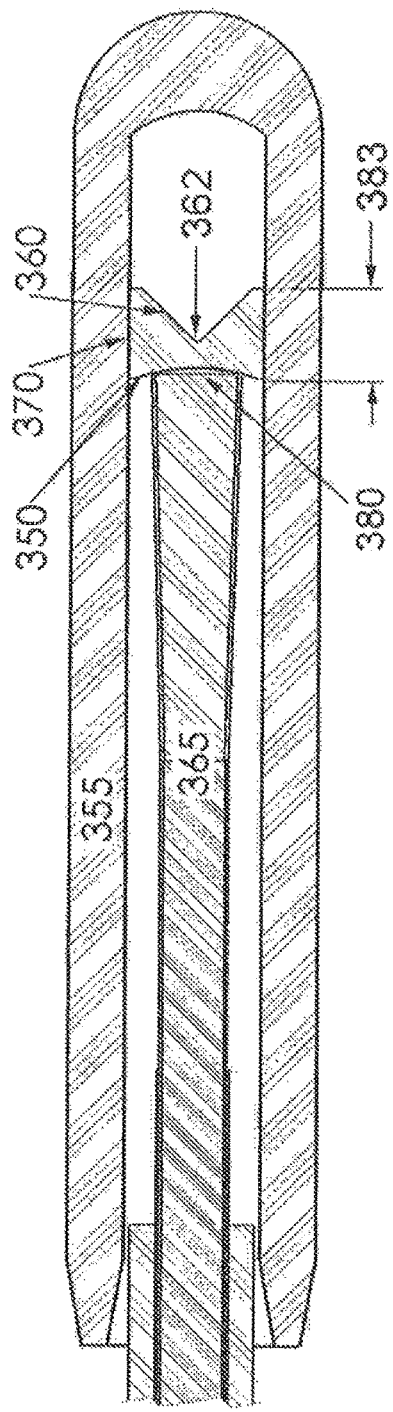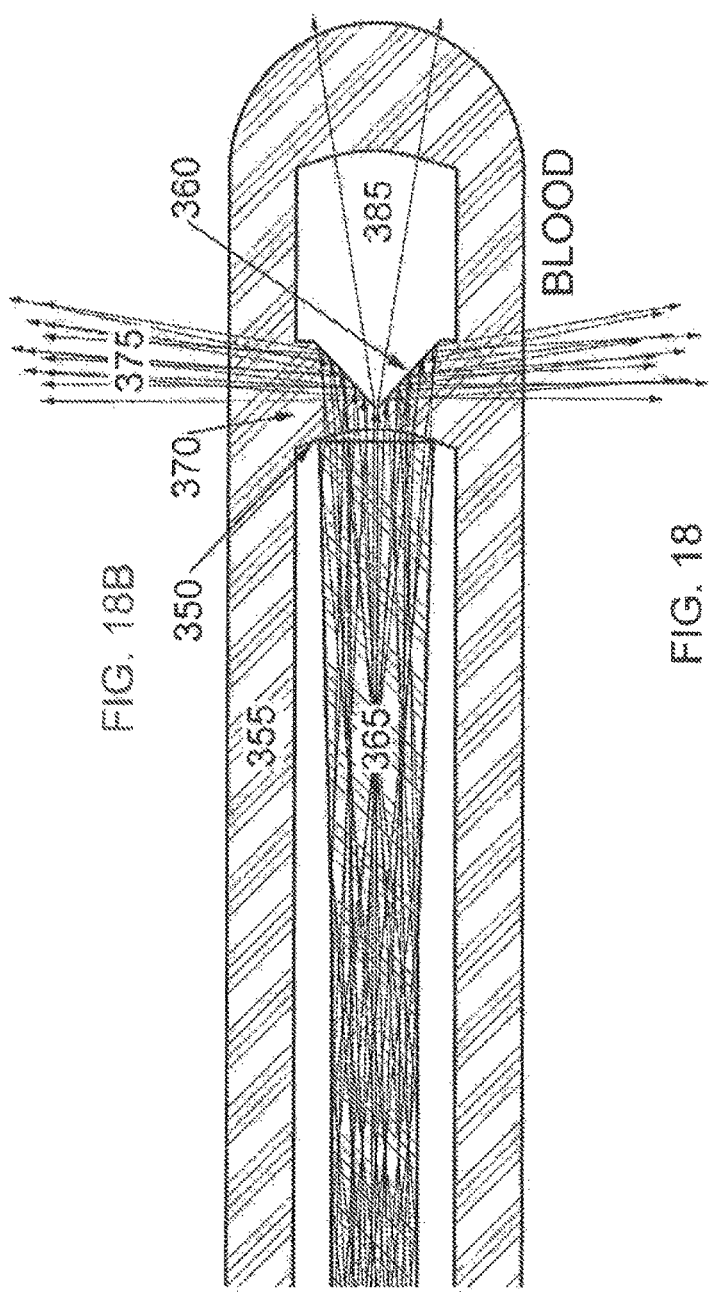

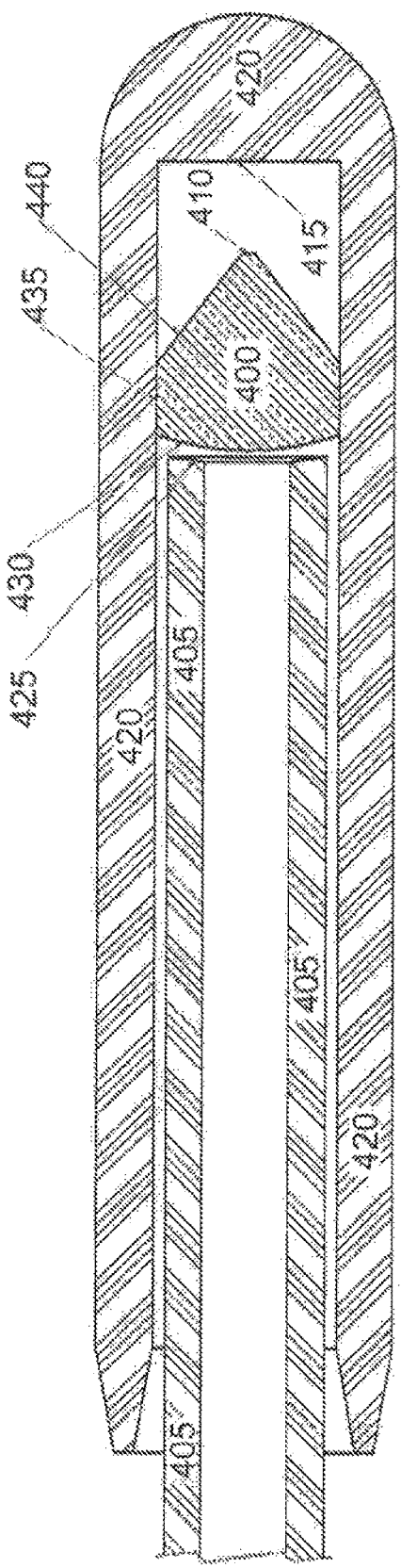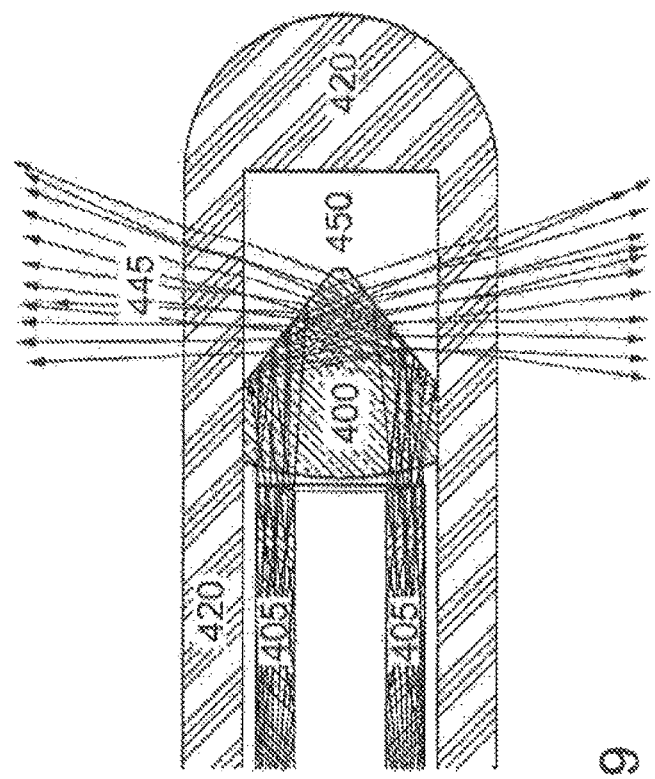
FIG. 19A  FIG. 19B  FIG. 19

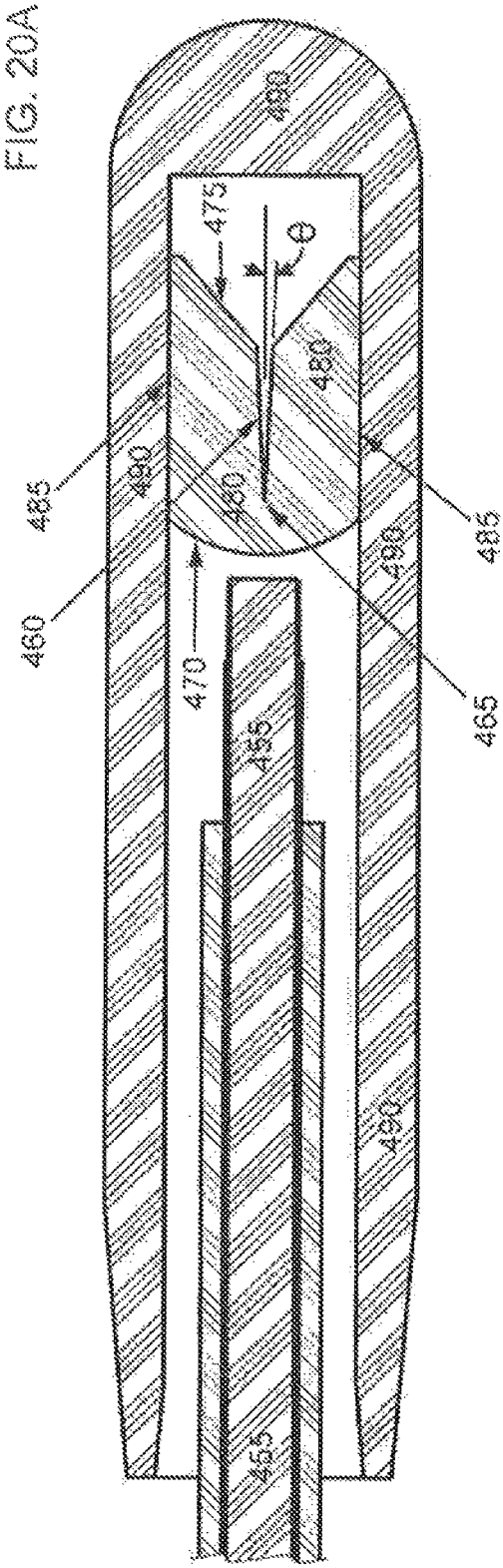
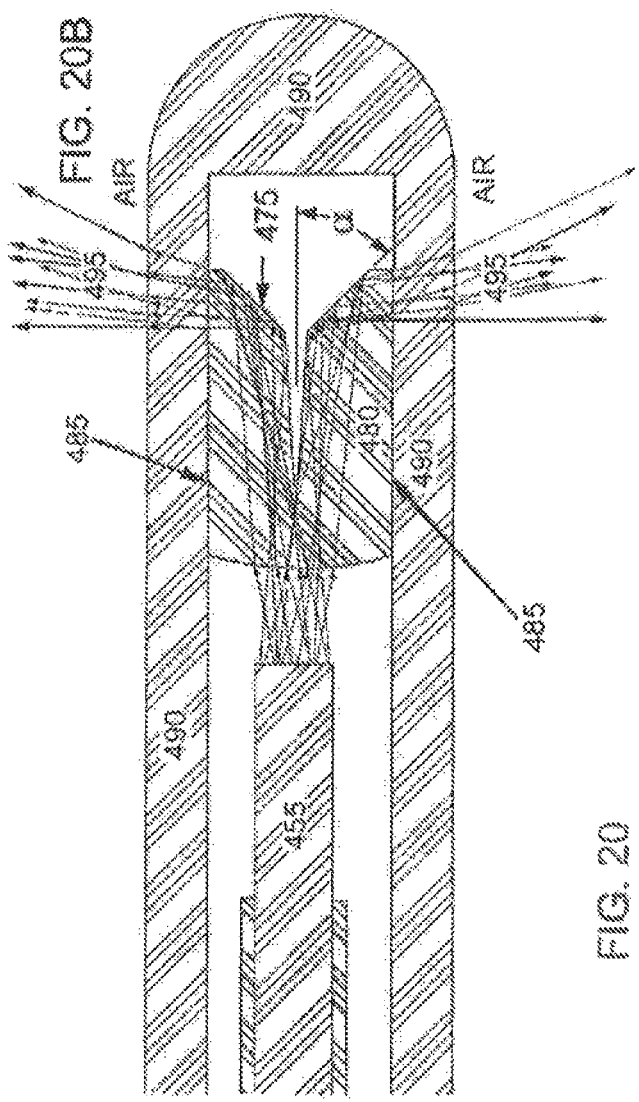

FORMING RADIAL EMISSIONS FROM OPTICAL FIBERS

CROSS-REFERENCE TO RELATED APPLICATIONS

This US patent application is a continuation-in-part from and claims the benefit of the U.S. patent application Ser. No. 16/122,982, filed on Sep. 6, 2018 and now published as U.S. 2019/0000549, which in turn is a divisional from U.S. patent application Ser. No. 14/944,266, filed Nov. 18, 2015 and now granted as U.S. Pat. No. 10,092,356. The disclosure of each of the above-identified applications is incorporated herein by reference.

TECHNICAL FIELD

This invention relates to devices and methodologies configured to modify a profile of a radiative output from a fiber-optic element such as to make the achieved modifications useful and advantageous in the treatment of various intracorporeal diseases with intense light (e.g., the radiative output from lasers), particularly endovenous and peripheral artery diseases.

RELATED ART

Fiber-optic elements structured to ensure lateral emission, radial emission, and diffusion of light at the output from optical fibers are utilized in a variety of light-based surgical procedures including laser interstitial thermal therapy, endovenous laser ablation, endometrial coagulation and ablation, endovenous thermal therapy, and photodynamic therapy. Additional surgical interventions have been proposed with the use of these modified output fibers including ablation, vaporization, and/or coagulation of tissue: for example, various treatments of hyperplastic prostate tissue, laryngeal tumors, and atherosclerotic and vulnerable plaques.

Structural modifications of optical fiber elements, including additions to an optical fiber that have been judiciously formatted to alter the axial output, typically utilize scattering elements to produce diffuse energy emission over significant lengths of fiber (distal-termini) in both rigid and flexible designs. Fiber optics structured to utilize scattering effects are generally very limited in total power-handling capacity due to the fact that such optics convert a significant portion of the photonic energy to thermal energy, and a reliance upon polymer matrices for carrying the scattering centers. (Such scattering modality outputs are referred to below as diffuse or diffusing light outputs or output emissions.)

The term "radial emission" has been used to describe an optical fiber light output ranging from the conventional, standard spatially-diverging within the limits defined by a high numerical aperture (NA) and a substantially axially-symmetric light output (corresponding to a flat polished terminating facet of an optical fiber), to light reflected by and/or refracted through conical surfaces. Broadly defined, "radial output" or "radial emission" optical fibers or optical fiber systems are those configured to produce a radial component if the term "radial" includes any off-axis emission (i.e., in this context any fiber output other than a truly collimated output has a "radial" component or components).

Alternatively, the term "laterally emitting" optical fibers is typically limited to optical fiber elements providing single- and multi-point off axis emissions. One example of laterally emitting fibers includes fibers with a series of notches on one side (see elements 31, 32, 33 in FIG. 4). Another example includes optical fibers launching light into stacked angularly-terminated segments of optical fiber, where the values of termination angles differ and begin at a critical angle for just a portion of the angular modes within the delivery fiber and progress all the way to the critical angle calculated for all angular modes carried within such fiber (FIG. 5).

A difference of philosophy exists within the art of the broadest surgical application of such fiber technology (for varicose vein surgery or endovenous laser treatment, ELT). In either case, the delivered to blood vessels laser energy is used to selectively damage vessels for post-surgical absorption. One camp of specialists advocates for indirect heating of veins (via heating the blood within the vein, often to the point of boiling) by firing laser energy into the blood-filled vessel while moving the fiber along the length of the segment under treatment. If position of the fiber delivering laser energy is maintained within the center of the vessel, the radiant output from the fiber remains relatively uniform and the speed of movement of the fiber is adjusted such as to account for variations in vessel diameter and shape: while this technique is discussed to minimize complications of overtreatment such as vascular perforation, it does appear to result in considerable thrombosis (blood clotting). Such treatment is generally carried out with a simple high numerical aperture (NA) and flat-polished output facet fiber with some provision for preventing fiber-tip-to-blood-vessel wall contact.

Another camp advocates for heating the vessel wall directly to avoid interactions of light with the blood to prevent post-operative complications from excessive thrombosis. It is with the latter camp that the use of a uniform and true radial emission from the optical fiber is most beneficial, because vessel perforations are more likely to result from irregular application of laser energy.

Numerous examples of radially and laterally emitting fibers have been attempted. U.S. Pat. No. 4,669,467 (Willett, et al.), for example, teaches stress-induced mode mixing for adjusting the light spot size and spot overlap of a plurality of fibers terminated within a transparent protective capsule, where the individual fibers may be arranged such as to point in slightly different directions, for the treatment of vascular tissue or obstructions thereof. The reference cites studies from the early 1980s, in which studies direct contact between optical fibers delivering laser energy within blood vessels occurred and resulted in thrombosis and vascular perforation. A series of related works—U.S. Pat. No. 4,718, 417 (Kittrell, et al.), U.S. Pat. No. 5,104,392 (Kittrell, et al.), U.S. Pat. No. 5,106,387 (Kittrell, et al.), U.S. Pat. No. 5,125,404 (Kittrell, et al.), U.S. Pat. No. 5,199,431 (Kittrell, et al.), U.S. Pat. No. 5,290,275 (Kittrell, et al.), U.S. Pat. No. 4,967,745 (Hayes, et al.), U.S. Pat. No. 5,192,278 (Hayes, et al.)—disclose additional utility including spectroscopic diagnostics, dosage control via feedback during surgery, and alternative constructions (including the use of additional optical elements within the protective capsule for altered illumination and collection patterns: a lens, a mirror, a holographic element, a prism, different lenses for individual fibers or groups of fibers and an acousto-optic deflector).

U.S. Pat. No. 4,842,390 ('390; Sottini, et al.) discloses a fiber optic device for angioplasty (FIG. 1) that utilizes a protective microcapsule 5 about the fiber output 3, where the capsule 5 is shaped 6 so as to produce a diverging annular output, or hollow cone, where the distribution of laser energy is further controlled by shaping the plastic clad fiber 1, in the illustrated case, as a cone tip 3. Sottini included a capillary 8 within the invention, providing communication between the cap interior volume, through the adhesive seal to the outside for the purpose of venting " . . . a dangerous pressure increase in the gas or air contained in the microcapsule" leading one to conclude that the efficiency of the radial emission was pool.

U.S. Pat. No. 5,093,877 ('877; Aita, et al., FIG. 2) similarly teaches a protective cap 11 or capsule about a fiber 10 that serves as a beam conditioning 'microlens', where the closed end 16 of the transmissive capsule shapes the fiber output. Aita describes a gold or other radiopaque material ferrule 12 around the bare portion of the fiber 13, fixed in position with epoxy 18 and describes alternative curvatures for the first lens surface 15 and second lens surface 16 as well as filling the space 17 with materials of different refractive index for shaping the output from the flat fiber tip 14: one embodiment appearing virtually identical to '390 with a flat polished fiber. Filling the volume 17 with a fluid would produce a dangerous pressure increase, as described by Sottini, even at moderate laser powers unless the fluid were exceedingly transparent at the laser wavelength used and the device did not warm with use. Further, the ability of the second lens surface 16, or any optical surface in contact with whole or diluted blood, to refract the laser light emitted by the fiber tip 14 is greatly reduced because the refractive indices for whole blood n=1.38) and dilute blood (n=1.35@ 20%) are relatively similar to that of fused silica (n=1.46), particularly in comparison to air (n=1.00).

Similarly, U.S. Pat. No. 5,231,684 ('684; Narciso, Jr., et al., FIG. 3) discloses a lens 20 mounted within the opening of the larger 21 of a pair of telescoping metal tubes 21 & 22 provided for redundant attachment to the optical fiber 23 buffer and cladding 24, where the space 29 between the lens curvature 25 and the fiber output 26 may be filled with fluid or elastomer having a similar refractive index as the fiber core and lens, thereby eliminating any refraction and therefore any function for the lens within the invention.

An abraded fiber core as a terminal diffusing segment of a surgical fiber is described in U.S. Pat. No. 5,019,075 (Spears, et. al.) teaches repair of physical damage to arterial walls during balloon angioplasty where light is intended to scatter in all directions along a length of the fiber that traverses the length of an angioplasty balloon along its axis.

U.S. Pat. No. 5,292,320 ('320; Brown, et al.) teaches lateral delivery or side firing fibers (FIG. 4) where the single bevel tip 34 known to the art is augmented with a series of progressively shallower notches 33, 32 and 31 in the fiber 30, aligned substantially parallel to the primary bevel tip 34 plane, for redirecting fractions of the light within the fiber off the fiber axis and substantially in the same direction. Alternative embodiments include notches with differing angles as well as a spiral and other groove cut into a fiber for redirecting at least a portion of the energy carried therein. Brown teaches an optional protective cap 35 that is anything but optional. U.S. Pat. No. 5,496,308 (Brown, et al.) continues '320 where temperature dependent radiation form tissue is also collected in the device for monitoring and control.

An attempt to reduce Brown '320 to practice was made in 1994 by this inventor and Brown, but was promptly abandoned as impractical to manufacture and unsafe to use. An alternative design FIG. 5 was devised using angle polished segments of fiber 36, stacked within an elongated capsule 37 and butt-coupled to a flat polished 39 optical fiber 38 to produce a similar effect as sought in '320, but the distribution of the output energy profile proved difficult to control and the project was abandoned (non-patented work).

Similar to Aita '877, U.S. Pat. No. 5,342,355 (Long) teaches a transmissive cap for shaping the output of flat tip and convex tip optical fibers housed within the cap for heating tissue directly with laser light as refracted by the tip, heating the tip with laser light with the heat conducted to the tissue and exciting a gas trapped between the fiber output and the inside wall of the tip to form a plasma.

A system for treating prostate tissue with CO2 lasers via urethral access (FIG. 6) was described in U.S. Pat. No. 5,468,239 ('239; Tanner) wherein a hollow waveguide 40 delivers energy across a space to a reflective cone 41 which redirects the radiation in 360° radial to the cone and orthogonal 43 to the waveguide longitudinal axis along which rays 42 are exclusively drawn.

U.S. Pat. No. 5,737,472 (Beranasson, et al.) teaches control of radial emission from a segment of fiber through differential defect generation in the fiber diameter, for example as produced by controlled sandblasting.

U.S. Pat. No. 5,908,415 ('415; Sinofsky) teaches a transparent, plastic tube which surrounds and extends beyond the distal end of a fiber, where the tube is filled with a silicone matrix containing light-scattering particles uniformly distributed therein. A reflective surface at the distal end of the tube serves to plug the tube such that light traveling from the fiber to the distal end of the tube is reinforced by the light that is reflected back from the reflective surface to produce a comparatively uniform light intensity along the length of the tube. Such devices have found utility in photodynamic therapy and other applications where low laser power is sufficient.

U.S. Pat. No. 6,398,777 (Navarro, et al.) teaches intraluminal contact between a fiber optic tip and a blood vessel wall, using laser energy from 200 μm to 1100 μm, but does also mention that the tip of the fiber may be rounded.

A method similar to Sinofsky '415, with elements of Brown '320 and its offspring echoed therein, is taught in U.S. Pat. No. 6,893,432 (Intintoli), where a tube affixed to the end of a fiber houses stacked segments of differential mixtures of transmissive and dispersive compounds providing successive bands of radial emission that may be tuned by altering the mixtures housed in the tube segments.

U.S. Pat. Nos. 7,270,656; 8,211,095; and 8,851,080 (Gowda, et al.) teach active cooling of diffusive fiber tips for laser interstitial thermal therapy where the tips are produced by "embedded scattering centers" and less than full 360° emission is controlled by "reflective means".

U.S. Pat. No. 7,273,478 (Appling) teaches away from radial emission for indirect heating of blood vessel walls via hot gas bubbles generated by axial output fibers, so long as those fiber tips are prevented from directly contacting the vessel wall by surrounding the fiber distal end with a ceramic spacer or, as described in U.S. Pat. No. 7,559,329 ('329; Appling, et al.), an expandable spacer such as a wire basket.

U.S. Pat. No. 7,524,316 ('316; Hennings, et al.) devotes a section to discussions of diffusing fiber tips stating therein, "The use of diffusing tip fibers for the treatment of varicose veins is unique and has not been previously described." '316 further teaches that shaped fiber tips are largely useless in direct contact with blood due to closely matching refractive indices essentially eliminating non-standard refractive output, and teaches the use of an internally threaded (diffusing) material screwed onto the fiber buffer as a diffuser, a ceramic or other scattering material in the form of a bead placed in the fiber output path within a transparent protective capsule housing both fiber and bead, and simply housing a cone-tipped fiber within a protective capsule and a rounded tip (orb) fiber with no protective capsule. Such capped cone tip fibers are in common use today.

U.S. Pat Appl. Pub. No. 2005/0015123 (Paithankar) teaches the use of diffusing tip fibers produced by a polymer or ceramic "cover" that includes a scattering material in the form of a cylinder about a fiber tip or a ball on the fiber tip to, " . . . overcome the index of refraction matching properties of the optical fiber and the adjacent fluid or tissue."

U.S. Pat. No. 7,386,203 (Maitland, et al.) describes diffuser tip fibers in considerable detail and modifies the related art by employing a shape memory polymer as the medium for carrying the scattering centers for diffusion, purportedly providing some control of that diffusion by way of the shape memory polymer substrate.

A transparent spacer/nozzle serving as a coaxial coolant conduit is taught in U.S. Pat. No. 8,435,235 ('235; Stevens) where the delivery fiber is recessed within the transparent spacer such that radiation is emitted through the spacer wall, through the nozzle opening or both as delivered by an axial fiber or cone-tipped fiber. The transparent spacer is prevented from contacting vessel walls in manners similar to '329. '235 also teaches a version of '239 (FIG. 7) where radial emission is accomplished via reflection from an inverted cone 45 placed distal to the axial output fiber 46, various means of centering the fiber assembly within vessel walls, a fiber assembly with an absorbing or scattering material placed within a fiber output path, a shaped tip fiber with an internal lumen for fluid conduction, etc.

In U.S. Pat. No. 8,257,347 ('347; Neuberger, FIG. 8) a radially distributed beam is described where reflections in all directions orthogonal to the fiber longitudinal axis is accomplished by removing a portion of the fiber buffer 49 to expose the cladding 53 and removal of part of the fiber core 50 producing a short, cladding only section 54 of fiber that terminates in a conical void 52 within the solid core 50. The hollow, cladding only section 54 is then plugging at the opening with a short quartz cylinder 55, preserving an air pocket 51 for the low refractive index such that light imparting the conical void in the core is redirected laterally, in all directions. As the drawing within '347 depicting this embodiment intimates (FIG. 5 surface 52, in the original drawing, is sketched as rough and ragged), producing such a structure with smooth and flat surfaces (a right circular cone as opposed to curved surface cones akin to a Hershey's Kiss) for efficient reflection is a challenging proposition and requires exceptionally thick cladding 53 (sketched as thicker than the fiber core in the original figure within '347); anything less than a highly polished surface at 52 will result in significant scatter and axial emission. Cladding is expensive, particularly when it is fluorine-doped silica, as it must be for '347 to be produced.

U.S. Pat. No. 8,285,097 (Griffin) describes a strategy similar to '347 that is also impractical for ELA (Endoluminal Laser Ablation) also known as ELT (Endovenous Laser Treatment), EVLT (EndoVenous Laser Therapy, Angiodynamics) and other, similar acronyms. As shown in FIG. 9, a glass clad 62 tube 60, or annular core fiber, is gently collapsed over the length of the tube until the inner diameter ceases to exist 66, thus forming a solid core to annular core fiber adapter. The open end of the annular fiber is chamfered 70 to redirect energy laterally while the solid end 66 is spliced 68 to the end of a clad 74, solid core fiber 72. The entire bare glass section is secured within a protective cap 76. Light from the solid core fiber is gently redirected into the annular core about the vanishing conical bore 64, encounters the critical angle chamfer 70 and exits as radial emission centered approximately at twice the chamfer angle. In one embodiment, near orthogonal performance may be obtained with divergence lower than the solid core fiber to which the solid to annular core adapter was fused but axial transmission remains problematic due to the chamfer 70 failing to extend completely across the annular core 75.

U.S. Pat. No. 5,242,438 ('438; Saadatmanesh, et al.) discloses a device that " . . . includes special beam splitter or diverging device . . . a transmitting end portion which has a frustoconical, annular configuration defining an annular end surface for emitting the laser radiation in a generally ring-like, cylindrical beam which is generally parallel to the longitudinal axis . . . " to avoid " . . . exposing the tip of the conical reflecting surface to the laser energy, and the surface can still function to reflect the radiation generally laterally of the axis . . . ". FIG. 10 illustrates this embodiment of the related art where the "special beam splitter" 78 is analogous to the "solid core to annular adapter" in FIG. 9, but without the beam turning chamfer 70 at the terminal ID and instead relying upon the metallic reflector 82 distal to 78. It is of merit to note that the placement of the special beam splitter 78 between the fiber 80 output face 88 and the surface reflector 82 serves no real function other than the purported avoidance of exposing the tip of the conical reflecting surface 82 to the laser energy 84. As such, this embodiment serves only to permit imperfections in the reflecting cone and in the process generates Fresnel reflections within the device at 88 and 90.

Other embodiments in '438 are also directed to steering energy away from the center of terminal conical-surface-based reflectors, including a concave conical pit in the fiber core akin to that in '347, produced with "a diamond drill" and a plurality of circumferentially disposed optical fibers or a ring output array. These strategies are necessary because directly illuminating a metallic conical reflector with the semi-Gaussian output profile of a laser driven optical fiber exposes the most difficult to prefect feature of the reflector, the cone point, to the highest energy densities. As with other related art, overheating remains a central concern in '438 due to the inefficiencies of methods used for redirecting light therein.

U.S. Pat. No. 6,102,905 (Baxter, et al.) teaches a variety of embodiments of low power photodynamic therapy devices, similar to those taught by Sinofsky in '415, that must be low power due to the low temperature liability of the "optical elements" identified therein, include gradient index lenses, such as GRIN lenses (SELFOC®) produced by NSG America, made of gradient doped (germanium) silica, "cylindrical disks" and "hemispherical domes" made of PTFE, ETFE, FEP and PFA fluoropolymers, etc.

An inverted or opposing cone for reflecting the axial remnants from cone-tipped fibers is described in U. S. Pat. Appl. Pub. No. 2009/0240242 ('242; Neuberger) along with a reprise of '320 and '308 where grooves are formed within the diameter of the fiber to produce a leakage pattern, a reprise of '347 where a hollow cone is machined in the end of an orb-tipped fiber, and combinations of hollow cones as well as auxiliary conical reflectors and simple axial output fibers protected by capsules or sleeves.

Generally addressing the deficiencies of cone-tipped optical fibers used in ELA treatment of varicose veins, including those housed within protective capsules, '242 teaches the addition of a secondary reflector 112 as depicted in FIG. 11. More completely, an optical fiber having a cladding 100 and a core 104 is equipped with a polished conical tip 110 where the angle of the cone is designed to reflect substantially all of the energy within the fiber core to angles significantly displaced from the fiber longitudinal axis. This does not occur for a simple cone tip fiber (FIG. 12) for a variety of reasons, one being imperfect cone tips 102 that allow emission of substantially axial radiation that, according to publication '242, will be intercepted and reflected by a second cone 112 made of quartz and sealed within the typical quartz protective capsule 106 found in much of the related art.

U.S. Pat. Appl. Pub. No. 2010/0179525 ('525; Neuberger) expands upon one embodiment within Pub. No. '242 and adds fiber centering mechanisms much like those disclose within Gowda, et al., and Appling. The single embodiment of Pub. No. '242 that appears to be expanded upon in the addition on FIG. 12 within 'Pub. No. '525 is not described within the text and is, as such, impossible to analyze. Notwithstanding this caveat, FIG. 12 in Pub. No. '242 appears to be a foreshortened version of one of the embodiments within related art '097, where the protective cap 76 to FIG. 9 is replaced by a flat window about the chamfered opening 70.

U. S. Pat. Appl. Pub. No. 2011/0282330 (Harschack, et al.) teaches a variation of '320 and '308 where a series of grooves on one side of a fiber, or a spiral groove encircling the fiber, is/are replaced by what amounts to be circumferential grooves, described in Pub. No. '525 as "truncated cones".

U.S. Pat. Appl. Pub. No. 2015/0057648 (Swift, et al.) teaches grooves and patterned grooves in a fiber for causing patterned leakage similar to the grooves in a sleeved and shaped fiber produced in our laboratory two decades ago and taught in U.S. Pat. No. 6,113,589 (Levy, et al) for endometrial coagulation or ablation.

SUMMARY

Embodiments of the invention provide, in part, an article of manufacture that contains an attachment structure dimensioned to be cooperated with an output facet of an optical fiber to accept light from such output facet and, upon propagation of through light through the attachment, to form an emission of the light directed radially with respect to an axis of the optical fiber element. The attachment includes an optical fiber having a core and a cladding, an input facet, and an output facet. There is a cone of an optical material is co-axial with the optical fiber and in optical communication with the output facet. The cone is dimensioned to receive light from the output facet through a base of the cone and to emit this light through a conical surface of the cone away from the axis. The optical fiber may include a fiber taper region (terminated with the output facet. (In one specific case, a core of the fiber has a circular cross-section in a plane transverse to the axis at every point along the fiber taper region such that a value of a core diameter at the output facet is larger than a value of the core diameter at any other cross-section of the fiber taper region.)

Embodiments additionally provide articles of manufacture that includes an optical-fiber protective cap dimensioned to be cooperated with an optical fiber to accept light from the optical fiber and, upon propagation of said light through the attachment, to output the light directed radially with respect to the optical fiber. In one implementation, the optical-fiber protective cap includes a tube having an axis, an open end and a sealed end; an optical element dimensioned as an optical lens element with an input curved optical surface facing the open end and an output optical surface facing the closed end; and a cone of an optical material that is co-axial with the axis and oriented such as to receive light from the open end through the output optical surface and a surface of a base of the cone and to transmit light through a conical surface of the cone away from the axis. Optionally, the optical element may be configured as a positive optical lens element. In a related implementation, the optical-fiber protective cap includes a tube having an axis, an open end and a sealed end; an optical element having an input curved optical surface facing the open end; and a conical surface positioned to receive said light from the open end through the input curved optical surface and to transfer such light through the conical surface away from the axis. (Here, the conical surface may be configured either as an output surface of the optical element itself—to limits spatial extent of the optical element along the axis—or a surface of a cone having a base surface facing the optical element and separated from the optical element by a gap.) In a related implementation, the optical-fiber protective cap includes a tube with an axis and having an open end and a sealed end, and an optical element with an input curved optical surface facing the open end and an output conical surface facing the sealed end. Here, the output conical surface is dimensioned to receive said light from the open end through the input curved optical surface and to reflect such light internally to the optical element and away from the axis. (In one specific case, the output conical surface may include a first conical surface portion having a first apex angle and a second conical surface portion having a second apex angle that is larger than the first apex angle and, optionally, have such second conical surface portion configured to form the light output by totally-internally-reflecting said light. Alternatively or in addition, the second conical surface portion may be structured to be located farther away from the input curved optical surface than the first conical surface portion. In substantially any implementation of an article of manufacture, the optical element may be formed irremovably connected at its radial boundary with an internal surface of the tube. Additionally or in the alternative, and in any implementation, the article of manufacture may additionally include a cannula connected to the protective cap, and/or a cannula-mount segment of a fiber-control device affixed to the cannula, and/or have an optical fiber cooperated with the fiber control device and inserted into said optical-fiber protective cap, and/or include a centering sleeve disposed about the optical fiber such that an output tip of the optical fiber is positioned proximally to the input surface of the optical element. (Optionally, the centering sleeve is then disposed about the output tip of the optical fiber.)

Embodiments of the invention also provide methods for propagating light through the articles of manufacture and, in particular, through the above-identified optical-fiber protective caps to form a radially-directed emission of light. In one specific implementation, the method includes accepting such light at an open end of the optical-fiber protective cap at the input surface of the above-identified optical element, transmitting this light through the above-identified cone of optical material, transmitting light through the conical surface of such cone to direct this light radially with respect to the axis and away from the axis. In one specific embodiment, for example, the method for propagating light includes receiving light at and inside an open end of a tube having a sealed end opposite the opened; and acquiring such light at an input optical surface of an optical element positioned inside the tube with the input optical surface facing the open end. The method additionally includes a step of receiving this light—upon transmitting the light through the optical element—at a conical surface located inside the tube; and reflecting said light at the conical surface through the conical surface away from the axis. In one specific case, the method includes a step of changing a degree of spatial divergence of the light upon said transmitting light through the optical element, and/or educing a degree of divergence of said light by transmitting the light through the input optical surface. Alternatively or in addition, the step of transmitting the light through the optical element may include transmitting the light through the optical element that has a spatial extent, along the axis, which is limited by the input optical surface and the conical surface. In a related case, the step of reflecting the light at the conical surface through the conical surface may include either reflecting the light internally to the optical element containing the conical surface, or reflecting the light internally to a cone containing this conical surface and separated from an output optical surface of the optical element by a gap. Furthermore, practically in any implementation of the method, the method may include a step of delivering this light through an optical fiber having an output tip secured in the tube and, optionally, passing this light inside a centering sleeve disposed about the output tip.

BRIEF DESCRIPTION OF THE DRAWINGS

For a more complete understanding of the disclosure, reference should be made to the following detailed description and accompanying drawing figures wherein:

FIG. 1 is a side view of an embodiment of related art, in which an early cone-tipped fiber housed within a transparent protective capsule (cap) to preserve conditions required for refraction of the output of the fiber and shaped to further refract that output.

FIG. 2 is a cross-section view of another embodiment of related art, where an axial firing fiber (flat tip) housed within a protective cap designed to shape the output of the fiber.

FIG. 3 provides an axial cross-sectional view of an embodiment of related art with an axially-firing fiber similar to that of FIG. 2, where the transparent protective cap is replaced by a metallic cap equipped with a terminal lens for shaping the output of the fiber.

FIG. 4 is a side view of yet another embodiment of related art, in which a lateral output fiber is designed to emit light at multiple points near the terminus by increasingly core invasive total internal reflection (TIR) notches and a standard TIR bevel at the terminus.

FIG. 5 is a side view of an embodiment of unpublished related art designed to correct the deficiencies of the operation of embodiment depicted in FIG. 4.

FIG. 6 is a side view of a structure including a conical metallic reflector at the distal terminus of a hollow waveguide, designed to radially emit $CO_2$ laser radiation.

FIG. 7 is a cross-section of a silica fiber optic equipped with a metallic cone reflector.

FIG. 8 is a cross-section depicting a conical void output fiber as taught by another implementation of related art.

FIG. 9 is a cross-section of related art '097 wherein a solid core fiber to annular core fiber converter is equipped with a chamfer at the annular core opening for total internal reflection, the solid core end spliced to a solid core fiber and the assembly protected with a quartz cap.

FIG. 10 depicts a related implementation, in a cross-sectional view, where a solid core to annular core fiber converter is butt-coupled to a solid core fiber at the solid core end to convert the standard conical output into an annular output for reflection at a distal metallic reflector.

FIG. 11 is a cross-sectional view of yet another related embodiment, in which the undesirable forward output of a cone tip fiber is said to reflect at a second cone of quartz fused within a quartz protective cap.

FIGS. 13A and 13B are ray-trace schematics adapted from publications of related art to illustrate of the complexity of reflections within bevel tipped round optical fibers.

FIG. 14 includes sub-FIGS. 14A and 14B that depict the spot sizes of light exiting optical fibers with varying output angle and divergence (FIG. 14A) and a plot of the energy distribution (FIG. 14B) within two of those spots.

FIG. 15 includes sub-FIGS. 15A, 15B and 15C that present partial cross-sections of an embodiment of the invention illustrating the components of an overall structure (FIG. 15A), a ray-trace of the calculated light output (FIG. 15B) of the embodiment, and a structural detail (FIG. 15C).

FIG. 17 includes sub-FIGS. 17A, 17B, 17C. FIGS. 17A, FIG. 17B and FIG. 17C are cross-sections of a related embodiment of the invention with calculated ray-trace schematics (FIG. 17B and FIG. 17C), illustrating the difference between a light-output pattern in air (FIG. 17B) and a light-output pattern in a biological fluid (FIG. 17C).

FIG. 18 includes sub-FIGS. 18A and 18B. FIG. 18A and FIG. 18B are cross-sections of an embodiment of the invention, without and with superimposed ray traces depicting the calculated light output, respectively.

FIG. 19 includes sub-FIGS. 19A and 19B and presents cross-sectional views of an illustrative embodiment, with (FIG. 19B) and without (FIG. 19A) superimposed ray traces depicting the calculated light output.

FIG. 20 includes sub-FIGS. 20A and 20B and presents cross-sections of a preferred embodiment, with (FIG. 20B) and without (FIG. 20A) superimposed ray traces depicting the calculated output.

FIG. 21A depicts a disposable version of an embodiment of the invention. FIG. 21B provides the cross-sectional view of the structure of FIG. 21A; FIG. 21C is a detailed view of the working tip of the device of FIG. 21A in a cross-sectional view; and FIG. 21D is an isometric view of the structure of FIG. 21A.

Figure 12:
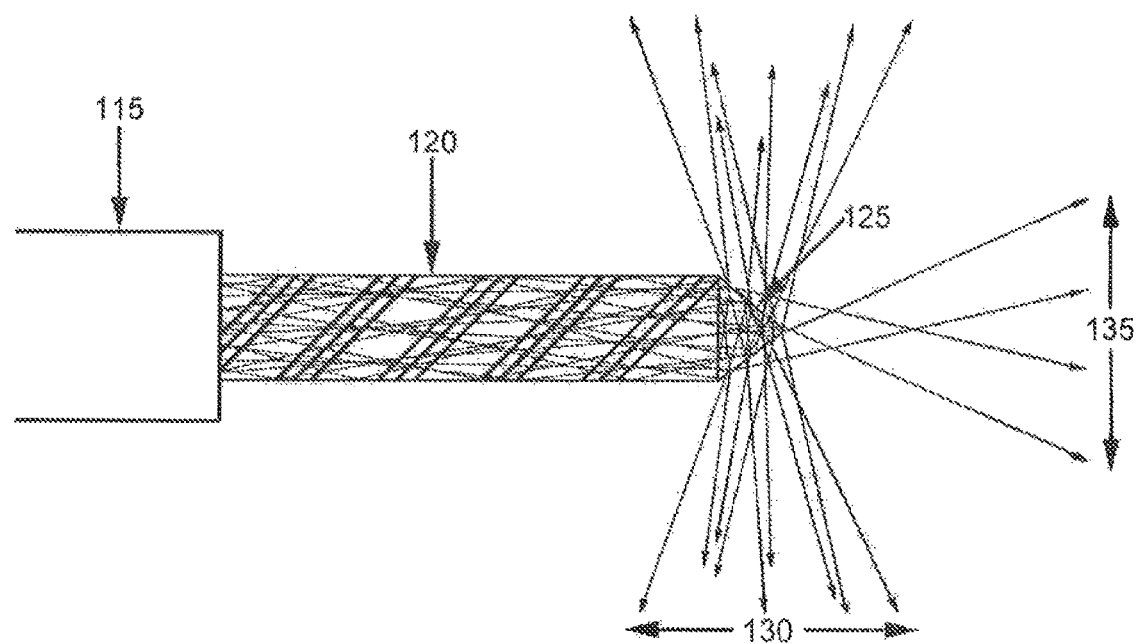
FIG. 12 is a ray-trace schematic illustrating a typical of cone tipped fiber output under the assumption of a defect-free conical surface and essentially infinitely small cone apex.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.

DETAILED DESCRIPTION

Radial emission or output, as these terms are interchangeably used herein, will be restricted to describing fiber emission that does not contain a significant axially-propagating component of the output light nor the angularly-emitted component that would normally be present in the radiative output from a flat polished terminating surface of the optical fiber of like NA when used within a similar environment. In other words, true radial emission, as this term is used herein, will refer exclusively to radial emission as described above, that spans 360° about the fiber circumferential outer surface with divergence that is lower than, equal to, or at least does not greatly exceed the divergence of light from a flatly polished facet or tip of the fiber of like NA when used under the same conditions Flat tip fibers, in conjunction with laser generators operating at wavelengths where hemoglobin absorbs light strongly, are commonly used in ELA surgeries to heat blood and indirectly coagulate or destroy damaged vessel walls in the treatment of varicose veins. Related art teaches avoiding contact between the fiber tip and the vessel wall for preventing perforations of the wall. Alternatively, wavelengths at which light is not strongly absorbed by hemoglobin have been taught to be employed for direct heating of vessel walls using radial emission optical fibers the structure of which ranges from including simple cone tips housed in quartz caps to numerous more complicated constructions designed to overcome the deficiencies of quartz capped, cone tip fibers. While all these constructs are treated as completely separate approaches within the related art and marketing materials, in reality there is a considerable component of the conventionally-utilized strategies expressed within the later surgery due to less than optimum spatial redirection of the light output of the employed fiber.

Minimization of the indirect heating effects when the direct heating methodology is employed is a common goal in the related art, as a skilled artisan knows. Shortening of optical paths from the fiber output surface to vessel walls are, therefore, advantageous for minimizing the interactions of the radiative output with blood or irrigation fluids, with the shortest path, understandably, being substantially orthogonal to the fiber axis at the output tip. Similarly, increase in efficiency of redirecting laser light towards the vessel wall target leads to requiring a smaller amount of laser energy to be used and, as a result, the reduction of the indirect heating effects during the surgery procedure.

The idea of the invention discussed below is aimed at forming a radiative output that is substantially orthogonal to the fiber-optic axis at high efficiency through the use of a radial emission optical component that is cooperated via adhesive with a simple, flat polished optical fiber (or fibers in the case of forming multiple radiative outputs).

Early attempts of related art to increase the divergence of light from optical fibers for use in ELA treatment of varicose veins included replacing flat-tipped fibers with ground and polished cone-tipped fibers such as that depicted in FIG. 12, for example. The results were disappointing for a variety of reasons. While cone-tipped fibers do produce widely diverging outputs, in air, this spatial characteristic of the radiative output is largely absent when the output medium is blood and/or saline irrigation fluids. Refraction and total internal reflection (both are involved in forming the cone-tipped fiber radiative output) depend on the different refractive indices of the media involved and on quality (smoothness, for example) of the boundary(ies) between these media. The close matching of refractive indices of the fused silica fiber core and of blood and irrigation fluids allows to largely eliminate the effect of cones, lenses, and other components. machined upon fiber tips ($n_{fused\ SiO2}$=1.46, $n_{air}$=1.00, $n_{blood}$=1.38, and $n_{saline}$=1.34), particularly where cone tips are juxtaposed with a fiber having a lower NA value that that of the flat tip output fiber these cone tips were intended to replace.

FIG. 12 presents a ray trace cartoon representing light propagation from a 0.22 NA fiber 120 that has the polymer coating 115 removed near the fiber terminus and the terminal tip is ground and polished to a cone 125. The angle of propagation of the output 130 with respect to the fiber axis is at least in part a function of the fiber's NA, the angle of the cone 125, and the refractive indices of the fiber core and the output medium in which the fiber is disposed.

At lower angles (with respect to the fiber axis) than those shown in FIG. 12, the undesirable output 135 (output of axial character) may be reduced, in theory, as the cone angle is reduced to angles that are close to those satisfying the criterion for total internal reflection (TIR) as defined by Snell's law for the filled fiber NA; however, the angle of the radial output (referencing the central ray within the diverging emission, for example the ray of light represented in FIG. 12 with an arrow having an arrowhead pointing to the label "130") is also directly proportional to the cone angle; the output of the central ray, relative to the longitudinal axis of the fiber, is equivalent to the total included angle of the cone, or apex angle. In practice—as opposed to theory—as cone angle is reduced (that is, as the cone is made physically longer compared with the diameter of the base of the cone), the amount of the undesirable, axial character radiative output is typically affected insignificantly and may actually even increase, as the sharper and more delicate points of the longer cones are more difficult to polish to minimal optical quality specifications (which include various parameters such as, for example, scratch-dig, irregularity, centricity).

Notably, a critical angle is classically calculated in accord with the Snell's law in relation to the normal to the refractive index interface and, as such, is the angle complementary to the angle(s) referenced herein and within the closely related art for side-fire fibers, also known as lateral delivery fibers. Where the critical angle is classically a minimum angle for total internal reflection (TIR), for such lateral delivery fiber product the critical angle represents a maximum angle.

Similarly to side fire fibers, cone tipped fibers also generate far more complex reflections and refractions of light that are expected upon cursory review. Excited modes within multimode optical fiber are not all the meridional modes, and actual modes are certainly not all 0th order meridional modes as depicted in most illustrations of related art showing the anticipated function of the fiber-optic device. In fact, for most multimode lasers used in target surgery (including the relatively low powered diodes lasers used in ELA), the majority of modes of light excited upon light propagation in the large-core fiber optics are skew modes: modes that do not cross the fiber axis at all. The use of meridional and $0^{th}$ order modes in large-core multimode fiber optics design is a gross over-simplification, at best.

Figure 13:
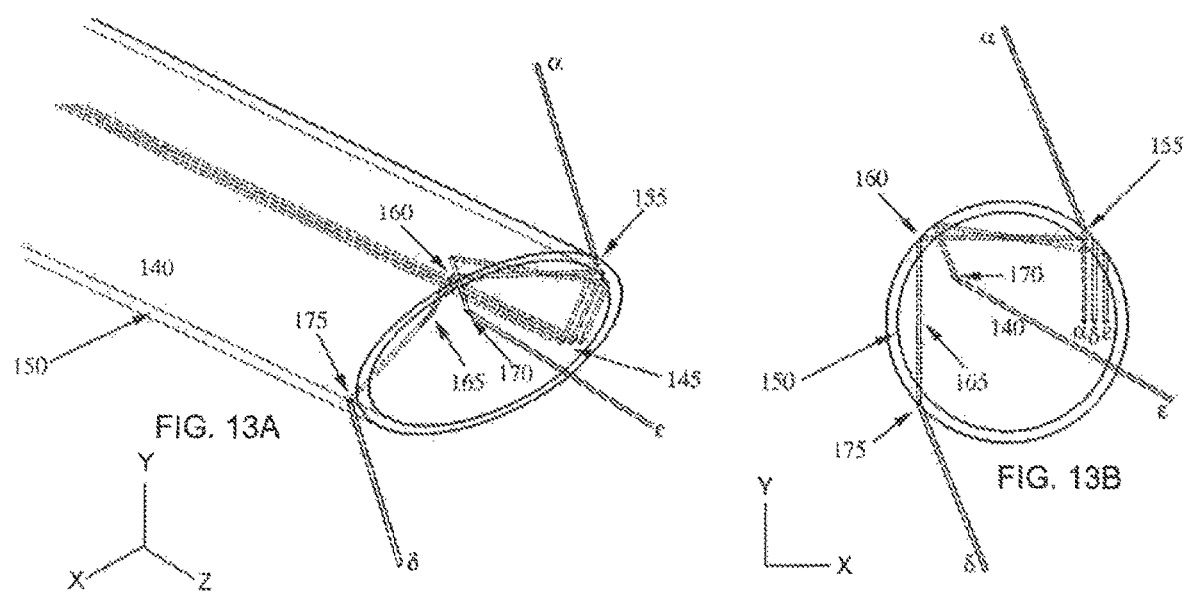
FIG. 13 includes sub-FIGS. 13A and 13B.

Two-dimensional ray tracing (the results of which are schematically illustrated in FIG. 13)—such as that used to produce the illustration of FIG. 12—also does not succeed to capture the complexity of light transmission within cone tips and bevel tips for a multimode fiber; two cartoons where three output rays ($\alpha$, $\delta$, $\varepsilon$) that are of a simple order mode propagating substantially parallel to the fiber longitudinal axis—are mapped to show their partial fates (Fresnel reflections upon exiting the fiber are not shown) in contacting a typical bevel-tipped side fire fiber such as the terminal reflector 34 in FIG. 4. FIG. 13A is an isometric view and FIG. 13B is an end view along the fiber axis. The core 140 and cladding 150 are treated as one, for simplification, because the refraction contribution at the core/cladding interface is a relatively minor perturbation for the purposes of the illustration. Rays ($\alpha$, $\delta$, $\varepsilon$) are parallel and encounter the TIR bevel at 145. The innermost ray, α, is refracted at the glass/air boundary at 155 because the angle of contact is too large for TIR. The middle ray, δ, imparts the glass/air boundary at an angle that is acute enough to totally reflect this ray to the opposite side of the fiber 160 where the contact angle is the same; then the ray is reflected again, but now in generally the opposite direction of the intended output. Ray δ next encounters the TIR face, again, at 165, reflects again and finds the glass/air boundary angle at 175 sufficiently obtuse to exit with refraction. The outermost ray depicted, ε, follows a path similar to that taken by δ but with more acute reflections within the fiber tip bending it to the TIR bevel glass/air boundary at an angle sufficiently obtuse to escape through the bevel face at 170. Refractions and reflections in the cone tips are more complex than the above-discussed in reference to the simplified and planar TIR bevel.

In short, the optical model of a cone tip is extremely complex and gives rise to highly spatially-distorted emissions—as compared with those anticipated in reliance on the oversimplified ray tracings, and similar in kind and quantity to those that are known and yet incompletely modeled for side-fire fibers. FIG. 13 presents an visual approximation, only, adapted from U.S. Pat. No. 5,428,699 (Pon), where it first appeared in support of the explanation of the almost 50% reduction in scatter (primarily backscatter) seen in side-fire fibers produced upon 1.4 CCDR fiber (Cladding to Core Diameter Ratio) with respect to 1.1 CCDR fiber: the larger total glass (cladding) diameter eliminates the more acute angles of incidence upon the glass/air interface, preventing secondary total internal reflections and reducing the amplitude of Fresnel reflections within the lateral output device. Such a solution is unavailable for cone-tipped fibers because the TIR surface is substantially centrosymmetric about the fiber longitudinal axis, which symmetry removes the very surface essential for application of the teachings of Pon. Furthermore, the curvature of the glass/air interface becomes progressively smaller for cone-tipped fibers, exacerbating the undesirable reflection issues briefly taught in the Pon patent.

While the addition of a transparent cap about the cone tipped fiber (typically fused quartz) serves to preserve the necessary refractive index difference for wider divergence (or off axis annular output) that is desirable for some approaches in ELA and other surgical interventions, additional refractions and Fresnel reflections at the air to cap interior surface adds additional complexity to the output. Furthermore, in contrast to idealized drawings within related art, the points of cone tipped fibers are not infinitely small, the walls of the cone are not optically smooth and regular, and the centricity of the cone with respect to the fiber longitudinal axis is relatively poor (most cone tips on fibers are not true right circular cones).

Sub-optimal optical surfaces on the cone-tipped fibers produce random light scattering that reduces the efficiency of treating the targeted vessel wall (or other tissue or disease states) and, instead, favors the formation of thromboses about the fiber output. Some chipping is ubiquitous near the apex of mechanically ground and polished cones, and the formed chips produce more spatially-concentrated scattering that can cause overtreatment of target tissue, thereby leading to vessel wall perforations. Laser-machined cone tips may be made quite smooth and although laser-formed cone walls typically do harbor low amplitude and long period surface ripples, these structural imperfections are typically too small to cause anything but slight phase shifts in wavefronts of the output light, which shifts cause no real surgical consequences. Laser-formed apices and edges are rounded to at least about 50 μm diameter (owing to diffraction-limited focus of the laser and heat conduction within the fiber tip), causing light leakage that is generally axial and highly spatially-divergent, which may contribute to formation of a thrombus at the distal terminus of a device, but concentrated errant emission is typically not a problem for laser-formed cone tips.

In the portions of the cones where cones narrow from the fiber's glass diameter to a minimum, conical voids (as taught in the '347 patent) offer a constant diameter of curvature for exiting rays in that the light exits through the original fiber's outer surface rather than through a diminishing cone, as is the case in positive cones. Axial leakage remains problematic for conical voids, however, due to the enhanced challenges in their formation as right circular vacancies with smooth wall optical surfaces, and in particular, production of small apices. Machining such concave voids to the very edge of a fiber core is exceedingly difficult on standard CCDR fiber, while increasing the CCDR of the fiber is costly in terms of both treasure and the critical dimension of fiber diameter.

Conically-shaped ends produced on annular core fibers are right conical frustum voids (a frustum—as commonly defined and understood—is a representation of a truncated cone or pyramid)—more easily envisioned and referred to by adopting the drafting term of "chamfer"—and, lacking an apex of the cone, there is no need to attempt forming one with minimal rounding. Smooth walls are easily produced with laser machining, even for bores in tubes as small as approximately 50 μm, and the angle of the chamfer may be precisely controlled over a very wide range. Although some low amplitude and long period surface ripples typically remain, the produced surfaces are highly reflective at the critical angle. A practical limitation of laser machining is that the bore must be open during the process such that gas flow may be used to prevent silica vapors from depositing within the bore beyond the chamfer. Two dimensional limitations also exist: the bore diameter needs to be larger than the diffraction-limited focal spot of the laser beam, in general, and the chamfer cannot extend all the way to the location defined by the outer diameter of the tube. Laser-produced chamfers are easily automated and highly reproducible process for forming reflective surfaces.

The idea of the present invention stems from the realization that strategies for blocking leaks of light employed by fundamentally flawed designs of related art yield suboptimal results during in surgical treatments: the conventionally-employed structures do not address the cause of the problem. Considering conversion of a beam of light with a circular cross-section (supported by the solid core fiber) to an annular cross-section beam (of a hollow core fiber, which is an essential element for conical void and chamfer surface reflectors, formation of the apex is a vexing problem for the former but is absent in the latter. For example, the chamfer on the solid-core-to-a-core-with-annular-cross-section converter segment depicted in FIG. 9 (from the fusion splice at 68 to the distal terminus at the chamfer 70) is produced on a straight tube under internal gas purge. The tube then is melted and drawn so as to collapse the bore in a controlled manner until it closes (as described in U.S. Pat. No. 5,512,078). The tapered bore is produced at a low angle relative to the longitudinal axis of the tube so as to minimally affect the NA within the converter segment, and the closure of the bore produces an apex that, while perhaps not infinitely small, is nevertheless smaller than a wavelength of light typically used in surgery and therefore does not scatter any perceptible amount of light.

Spatial distortions of the desired radiative output, cause by reflection and refraction of light, similar to those in side-fire fibers, FIG. 13, are still a problem with the annular converter solution disclosed in U.S. Pat. No. 8,285,097 (the '097 patent) and the fact that the chamfer TIR surface cannot extend to the edge of the glass diameter, thereby producing axial emissions that are quite similar to those seen with cone tipped fibers. CO2 laser ablation can machine chamfers to within approximately 200 µm from the outer edge of a tube 75 without much difficulty, and with great care (and extraordinarily long process times) the TIR surfaces may be extended to within about 100 µm from the edge of the glass before heat conduction and melt surface tension dominates to join the outer and inner surfaces in a meniscus. The drawings produced in the '097 patent clearly outline and represent this practical issue.

Another practical problem is that the cladding on the glass tube cannot be thicker than approximately 10 µm without adversely affecting the fusion splice at the solid-core-to-annular-core converter junction. The core of the solid core fiber should be larger than the core of the annular converter at the junction to avoid excitation of "cladding modes", or rays are confined by the cladding/air interface rather than the core/cladding interface. Any modes capable of exiting the annular-cross-section core within the non-chamfered annulus of cladding will emit with a generally axial orientation. If it is removed prior to fusion splicing, thicker cladding may be used on the annular converter segment, but this strategy further increases costs of both raw materials and processing. In short, addressing the axial emissions due to incomplete chamfer diameters causes problems in fusion splicing (or otherwise coupling) and device costs rapidly increase.

Notwithstanding cost issues, dimensional constraints obviate the teachings of the '097 patent for ELA and more dimensionally-restrictive surgical applications. In FIG. 9, the end of the fiber 72 that conducts energy from the laser to the annular converter segment is depicted as a standard, flat polished tip, but this is not truly the case for embodiments depicted in the original '972 patent. The conducting fiber must be up-tapered prior to joining with the annular converter because the converter both demotes propagated modes to lower angles at the outer diameter and promotes modes to higher angles of propagation at the inner diameter, where the inner diameter is dominant. Without first demoting the highest order modes within the up-tapered fiber segment, some mode angles presenting within the converter segment will not be contained. The length of bare, fragile glass that must be protected by the transparent quartz cap is exceedingly long with the addition of a fiber taper and the total diameter of the device within the cap is several times larger than the base fiber diameter, exceeding dimensional constraints for even the most liberal of surgical applications.

For the remaining portion of the discussion, a distinction is made—and best attempts are made to maintain this distinction—in using the terms "cone" and conical surface". The term conical surface is defined in line with a conventional understanding of this term in geometry—as a surface formed by the union of all the straight lines that pass through a fixed point—the apex or vertex of the conical surface—and any point of some fixed space curve—the directrix, which that does not contain the apex. The directrix that is practically-applicable to the subject at hand discussed here is a planar curve (the one drawn in a plane) and, more specifically, a circumference of a circle or ellipse. In comparison, the term cone refers to as a solid object bound by a conical surface and a portion plane (in which such directrix lies) subtended by the conical surface. Such portion of the plane is referred to herein after as a base of the cone. Accordingly, a cone is a distinctive three-dimensional solid body that has a flat surface and a curved surface, pointed towards the top (the apex or vertex). Additionally, the terms "positive cone" and "negative cone" (and, similarly, "positive conical surface" and "negative conical surface") are used to serve to simplify descriptions of the various embodiments. Feature 125 in FIG. 12 and feature 110 in FIG. 11 are examples of a surface of a positive cone (or, a positive conical surface; that is, the one in which a solid material of the cone surrounds the axis of a conical surface between the apex and the base of the cone, while the material surrounding a portion of the axis of the conical surface separated from the basis by the apex is not solid material). Surfaces 52 in FIGS. 8 and 70 in FIG. 9 represent surfaces of a negative cone (or, negative conical surfaces—that is, the ones in which the distribution of materials is reversed as compared to that of the positive cone). The "special beam splitter" 78 of FIG. 10 is neither a negative cone nor a positive cone in that its purpose is merely in support of subsequent redirection of the laser energy, much as is 64 of FIG. 9. Many of the disclosed embodiments will involve fusion of negative cone output surfaces to the inside diameters of protective caps for greatly reducing or even eliminating the undesirable scattering that plagues lateral emission devices of all kinds, as depicted in FIG. 13, without suffering the adverse consequences regularly encountered in solutions involving on-fiber fusion (as discussed in U.S. patent application Ser. No. 14/578,739, filed 22 Dec. 2014, the disclosure of which is incorporated by reference herein).

Improvements to performance in radial fiber designs are not limited to the elimination of sources of disorganized and organized scattering (although this remains an ultimate goal). FIG. 14 illustrates the importance of divergence and the angle of emission to irradiance from circumferential or radial emission fiber assemblies. In FIG. 14A, four beams are shown for comparison using a side-fire (single source) emission for clarity, where emitted beams are normalized to an initial 1 mm diameter. The beams terminate on the "varicose vein" innerwall 182. Beams 184 and 186 deliver the central rays at 90 degrees with respect to the axis of the vessel 181 axis, while beams corresponding to 185 and 187 are centered on lines inclined with respect to such axis at 45 degrees.

Comparison between the beams producing spots 184 and 185 illustrates the effect of the emission angle, only, upon irradiance: both beams diverge to the same degree. Treatment area 184 is 8.12 mm$^2$ while treatment area 185 is about 2.5-fold larger (at 20.14 mm$^2$): irradiance is reduced 2.5-fold at 45 degrees with respect to the axis versus 90 degrees. FIG. 14B is a heuristic plot illustrating the flattening of the beam profile in area 185 as compared with the area 184. Points A, B, C, and D are provided for referencing positions between FIG. 14A and FIG. 14B. The irradiance plots are relative, not absolute, but serve to demonstrate that the diameter E-E of the orthogonal treatment beam 184 is actually larger than the diameter F-F of the beam 185 propagating at a more acute angle (contrary to the initial impression) because attenuation and spatial dilution of the acute angle beam 185 reduces much of the irradiance to sub-therapeutic levels (see the dashed line).

Additionally—and considering again FIG. 14A—the beam producing spot 187 diverges twice as much as the beam producing spot 186. The combined effect of doubling the divergence rate and reducing the delivery angle from the optimal 90 degrees to 45 degrees causes the treatment area 186 to be about 5.91 mm$^2$ and the area of the spot 187 to be 46.46 mm$^2$ an 8-fold increase in the area of the spot for an 8-fold reduction in irradiance. A great deal of the laser energy within the beam producing area 187 is lost to absorption in blood, even for laser wavelength within the so-called "therapeutic window", variously defined as spectral regions as wide as 600 nm to 1300 nm and as narrow as 700 nm to 900 nm, where blood and water have absorption minima (also referred to as the "optical window", the "near IR window" and the "biological window").

One embodiment of the invention structured to reduce axial leakage from the laser-formed positive cone optical components is depicted in FIG. 15. Here, a (for example, fluorine-doped) silica clad, silica core fiber 200 is tapered to approximately twice its original diameter forming an up-tapered terminus 205 over a length of a few millimeters (as shown in the Figure—about 5 mm). The up-tapered terminus can have a length 207 that is about 3, 4, 5, 10, 15, or 20 times the core diameter 201; or a length 207 in a range of about 3 to about 20 times the core diameter 201. In some instances, the up-tapered terminus length 207 can be about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The end of up-tapered terminus 205 is laser machined to a cone-tip 211 with an apex angle 212 of approximately 90 degrees. In one instance, the apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°— depending on the specific implementation. Notably, the term "apex angle" refers to the maximum angle within a cone apex. Geometrically, the apex angle can range from about 1° to about 179°. In a positive cone the apex angle is "within" the substrate forming a cone whereas in a negative cone the apex angle is "outside" of the substrate forming a cone (e.g., in the space about the substrate).

Modes of laser energy propagating at higher angles within the fiber 200 are converted to lower-angle modes within the up-tapered terminus 205 such that the vast majority of rays imparting the cone wall 220 are totally reflected to the opposing wall (where the angle of incidence is such that the rays exit in the desired direction 235). In up-tapering the fiber, the cladding at the now-larger terminus is about twice as thick. Preferably, the up-tapered terminus 205 has a maximum taper diameter 206 that is at least 1.5 times the core diameter 201, more preferably about 1.5, 1.6, 1.7, 1.8, 1.9, 2.0, 2.1, 2.2, 2.3, 2.4, 2.5, 2.6, 2.7, 2.8, 2.9, or 3 times the core diameter 201, depending on the specifics of a particular implementation to produce the situation when the rounding of the edge 210 does not leak light significantly (because such rounding is contained primarily within the cladding when the indicated diameter ratio is observed). While the rounded apex 215 may continue leaking the energy in a generally axial direction 240, the amount of light lost due to such rounding is substantially smaller than— approximately one fourth of—the amount lost for a similar tip formed on the base fiber, without tapering (as a function of the reduction in the fraction of the cross-sectional area of the output occupied by the rounded apex).

In one specific example, depicted in FIG. 15A, the radial emission optical fiber termination can be implemented from a 400 µm core, 1.1 CCDR fiber and fitted with a 0.9 mm bore cap 225 having an outer diameter of 1.6 mm and a length of just over 1 cm: a size well within the dimensional requirements for ELA applications. The protective cap inner diameter conveniently accepts the nylon fiber buffer 230. When affixed (for example with an appropriate medical grade adhesive), the bond between nylon and fused quartz is exceptionally strong and reliable. FIG. 15B illustrates the radial output of the device (modeled in air) that is almost orthogonal to the fiber axis and of reduced divergence (as compared with that from the unmodified fiber 200 equipped with a flat polished tip and neglecting refraction at the cap surfaces). In practice, Fresnel reflections at the inner cap surface contribute to considerable scatter within the output exceeding the depicted primary ring. This radial emission optical fiber termination device can be adapted for use in coronary and cerebral arteries by, for example, employing core fiber with a smaller core diameter and including a lower ratio up-taper.

Figure 16A:
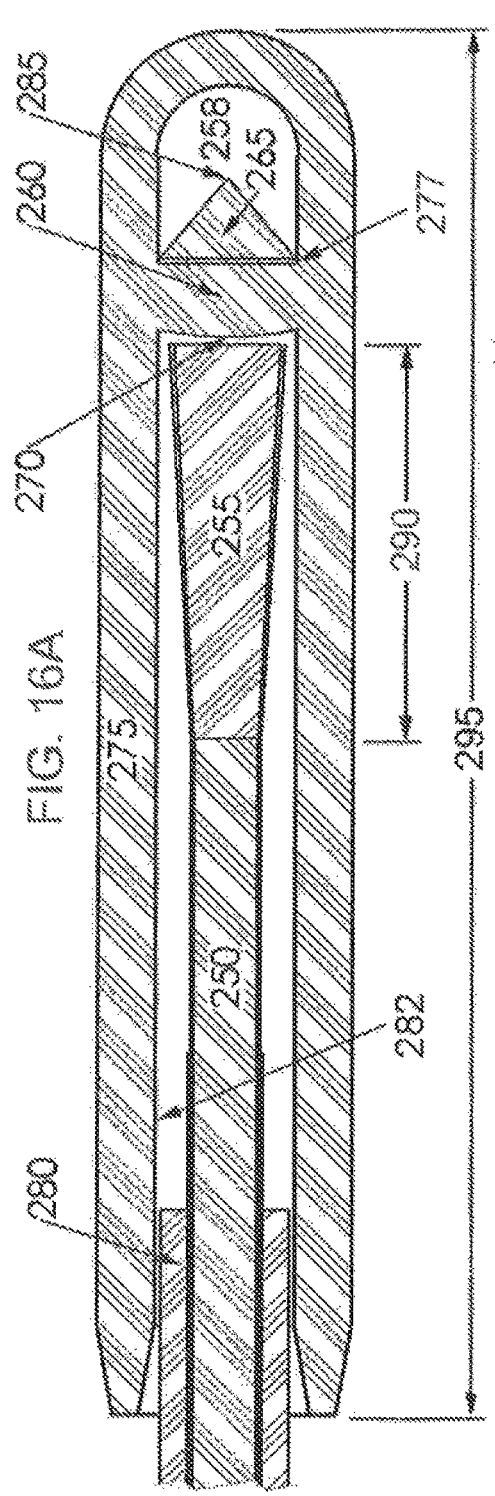
FIG. 16 includes sub-FIGS. 16A and 16B that depict cross-sections presented at two geometrical scales, with and without calculated output ray traces, of one specific embodiment of the invention.
Figure 16B:
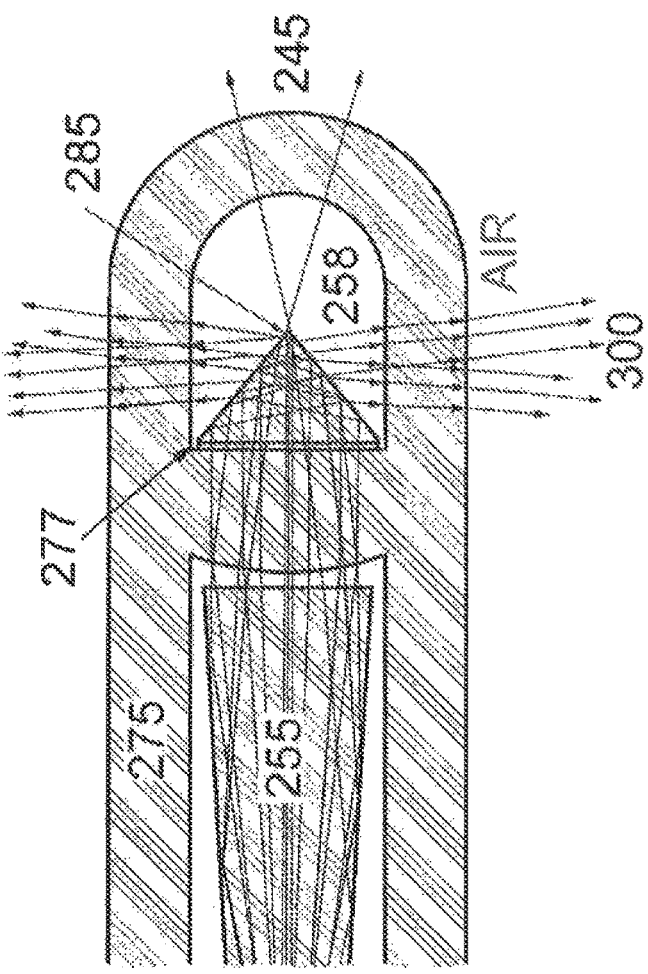

A related embodiment of a radial emission optical fiber termination component is depicted in FIG. 16. The structure of FIG. 16 is similar to that in FIG. 15 but, preferably, offers a measure of improved performance within similar or smaller dimensions and affords superior cap retention for enhanced safety in arterial applications. As shown, the radial emission optical fiber termination, preferably, includes a fiber cap 275 (that contains a glass tube and an optical element 260 bisecting the glass tube). As shown, the glass tube 275 can include an open end adapted to receive an optical fiber 250 and a closed end. In a non-limiting example, the optical element 260 may be made at least in part from fused quartz and/or fused silica and/or plastic material, have an input face or facet 270 proximal to the open end of the glass tube, and be cooperated with a conical surface 265 facing the closed end of the glass tube. This cooperation can be structured in two fashions. In one case, the conical surface 265 may be configured as part of a stand-alone cone element 266 that is spatially-independent from the element 260 and separated from an output facet of the element 260 by a gap 267 (as shown in FIGS. 16A, 16B). Alternatively, the conical surface 265 can be itself a second surface (output face) of the element 260 opposite to the input face 270 (in which case the optical element 260 is spatially limited along its axis by the surfaces 270 and 265, and there is no gap 267; not shown).

The input face 270 of the element 260 can be configured as a flat face, or a face defining a non-zero optical power (in which case a degree of spatial divergence of light is changed as a result of propagating of light through the input face 270) such as a convex face, a concave face (see, for example, FIG. 18), an annularly-shaped face, or a combination thereof. In one instance, the element 260 may generally be configured as a convex lens, while in another instance—a concave lens.

The diameter of the optical element 260 (as viewed down the axis of the glass tube) may be chosen to be substantially the same as the internal diameter of the glass tube, for example, about 0.1 mm to about 10 mm, about 1 mm to about 4 mm, or about 1.5 mm to about 3 mm, depending on the specific implementation. That is, the optical element may be fused to an internal wall of the glass tube in one specific case, to form a single/unitary piece (without limitations—of glass, fused quartz, or fused silica). The axial length measured from the input face 270 through the optical element 260 to the apex 285 of the conical surface (whether or not the conical surface belongs to a stand-alone cone appended to the optical element 260 or a surface of the element 260 itself) is about 1, 2, 3, 4, or 5 mm, and preferably shorter than 5, 4, or 3 mm.

In one instance, the conical face 265 is a positive conical surface formed from large diameter (roughly 0.9 mm), drawn silica rod with an apex angle of about 90 degrees, and corresponds to an almost perfect right circular cone. In another instance, the apex angle is in a range of about 70° to about 115°, about 70° to about 110°, about 70° to about 105°, about 70 to about 104°, about 70 to about 100°, about 75" to about 104°, about 75° to about 100°, about 80° to about 104°, about 80° to about 100°, about 85° to about 104°, or about 85° to about 100°.

The conical surface 265, preferably, further includes very smooth surfaces as opposed to those produced upon the ends of far less true rotating and tapered fibers, particularly where cones are formed by mechanical grinding and polishing. (Fiber is chucked upon the buffer to minimize the length of bare glass such that the relatively high buffer eccentricity is limiting for the formation of centrosymmetric cones.) Although the apex 285 may be formed rounded, better centricity produces a smaller apex than that upon the device in FIG. 15 such that the undesirable axial emissions 245 are further reduced.

The radial emission optical fiber termination component can additionally or in the alternative include an optical fiber element 250; in one non-limiting case such optical fiber element may include a polymer clad portion and a silica core. Preferably, the output of such optical fiber element is positioned within the open end of the glass tube and proximally to the input face 270 of the optical element 260. In one instance, the optical fiber element 250 is complemented with an up-tapered terminus 255. The up-tapered terminus 255 (e.g., formed upon the modification of a portion of the standard 1.1 CCDR fiber element 250) may be similar to that discussed in reference to another embodiment but be of shorter length 290. In one instance, the up-tapered terminus 255 can have a length of about 1.5, 2, 3, 4, 5, 10, or 15 times the diameter 201 of the core of the optical fiber element 250; or a length 290 in a range from about 1.5 to about 15 times the core diameter 201. In some instances, the up-tapered terminus length 207 can be about 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The fiber 250 may carry a polymer (e.g., nylon) coating or jacket 280 that is affixed (e.g., adhesively) to the internal surface 282 of the glass tube 275.

In one example, the shorter length up-taper terminus 255 may be utilized with a lens element formed by a convex input surface 270. This combination of up-tapered terminus and convex surface 270 reduces the overall divergence of the beam of light propagating therethrough while, at the same time, facilitating a formation of the light output 300 the central portion which is propagating at substantially right angles (that is, substantially truly radially) with respect to the longitudinal axis of the optical fiber.

When the surface 270 is convex, the focusing effect of the so-defined lens element 260 coupled with a diameter of the taper 255 (that is smaller than the diameter at a base of the conical surface 265) substantially completely eliminates any possibility for axial output emissions of light due to rounding at the outer edge 277 of the cone. Fresnel reflections at the cap wall remain somewhat in operation of this embodiment and new Fresnel reflections may occur at the input surface 270, but the former largely overlap the desired output (owing to the essentially orthogonal angle at which light 300 is outcoupled) and the latter are very diffuse and propagate proximally about the fiber, away from the surgical treatment area.

At least a portion of the optical element 260 between the input and output faces of such element may be fused within the protective cap 275, sealing a low-vacuum, a high-vacuum, and/or biocompatible gas-based atmosphere within the sealed space 258. In the example of FIGS. 16A, 16B, for example, the sealed space can be considered a "bubble" 258 between the closed end surface of the tube and the optical element 260. (In the same example, the stand-alone cone element is placed in the sealed space or bubble 250 with the base of the cone element facing the output face of the optical element 260.) A low-vacuum bubble can be formed at a pressure between about 750 Torr and about 25 Torr; alternatively, a high-vacuum bubble can be formed at a pressure lower than about 24 Torr. Preferably, the pressure within the bubble 258 is lower than 700, 600, 500, 400, 300, or 200 Torr (i.e., a low-vacuum). In a related instance, the bubble 258 includes a gas selected from nitrogen, argon, helium, a fluorocarbon, and a mixture thereof at a pressure lower than 700, 600, 500, 400, 300, or 200 Torr (i.e., a low-vacuum and including a biocompatible gas). Preferably, the cap is annealed prior to assembly, reducing the potential for stress-fracturing during thermal cycling in surgery. In a particularly preferably instance, the taper 255 is shorter than 3 mm, the overall length of the protective cap 275 may be reduced to less than 1 cm while not compromising the excellent strength and strain relieving bond between the nylon buffer 280 of the fiber and the inner wall of the cap 275.

In another related implementation, schematically illustrated in FIGS. 17, 18, the conical surface of the optical element bisecting the embodiment of the protective cap is structured as a negative conical surface 345 or 360. Such negative conical surface is dimensioned to spatially limit the corresponding optical element (shown as 320 in FIG. 17). The input surface or face of the protective-cap-bisecting optical element may be dimensioned as either concave or convex. The negative conical surface includes an apex angle of approximately 90 degrees. In another instance, the apex angle is in a range of about 70° to about 115°, about 70° to about 110°, about 70° to about 105°, about 70° to about 104°, about 70 to about 100°, about 75° to about 104°, about 75" to about 100", about 80° to about 104°, about 80" to about 100°, about 85° to about 104°, or about 85° to about 100°.

The negative conical surface can be made by micromachining into a cylindrical segment of the used material (in a non-limiting example—glass, fused quartz, fused silica, and/or plastic).

Referring again to FIG. 17, longer solid cylindrical elements may be preferred by nature of machining processes where the contact area between micromachining collets and cylindrical materials is higher, providing superior rotational symmetry. This machining precision consideration must be balanced by considerations of the desired divergence of light interacting with such surface. Where light within the solid cylindrical element 320 is diverging, axial length of the conical surface must necessarily be shorter to ensure the bulk of the fiber output imparts the distal optical surface 345 without overfilling the optical aperture of the optical surface. Where up-taper 305 and lens-forming input surface 343, and lenses on tapers (not illustrated) are used, spatial divergence of light propagating therethrough is greatly reduced and some degree of convergence may exist for short distances within the optical element 320, permitting a somewhat longer segment(s) to be used. In preserving the outer cylindrical shape of the optical element 320, negative conical surface offers superior conical symmetry over a positive cone or positive conical surface considered in reference to FIG. 16A.

Yet another consideration remains, however, that limits in practice the length of the cylindrical optical elements dividing the hollow of the tube 250, 315: the overall device rigid length (such as length 295 in FIG. 16A). Longer protective caps 275 are more susceptible to damage and more difficult to pass through endoscopic working channels. Leverage about a flaw located approximately in the center of the cap length should be minimized, also favoring shorter cap length. Optical, mechanical and endoscopic compatibility considerations limit the length of cylindrical optical elements to a maximum of approximately 5 mm for surgical applications, where non-surgical applications may well permit considerably longer and larger diameter elements to be considered.

As the negative conical surface 345 (FIG. 17A) cannot be easily maintained to the very edge of the cylindrical segment (e.g., due to fragility of the material and thermal distortion), it may be preferred to form a radial emission optical fiber termination with a negative conical surface that is larger in diameter than that of the positive version (FIG. 16; visible and intended to be indicated in the Figures by comparing the gap between the fiber buffer 310 and the cap 315 bore wall in FIG. 17A and the fiber buffer 280 and the cap 275 bore wall in FIG. 16A). The centricity advantage for the negative conical surface is somewhat offset by the fact that precision in maintaining a constant cone angle is far higher for positive cones versus negative cones.

As the diameter at the base of the negative conical surface is often smaller than the diameter at the base of a positive conical surface (or, of the base of the positive cone, in a related case), when the internal diameter of the tube is constant, the emissions from the optical fiber must be correctly reflected off of a smaller target when the negative conical surface is used. Accordingly, the ratio of the maximum diameter of the up-tapered termination 305 to the internal diameter of the tube with a negative cone (negative conical surface) is smaller than the ratio of the maximum diameter of the up-tapered termination to the internal diameter of a tube with a positive cone (positive conical surface). Additionally, the linearity of the conical surface itself limits the maximum off axis angle output 330 that can be achieved; preferably, the divergence in the output from a radial emission optical fiber termination with a negative cone (or conical surface) is higher than that of one with a positive cone (or conical surface) and some small amount of axial leakage 355 remains.

Because the surface area interaction of the parts during fabrication is greater when manufacturing an embodiment employing a negative cone or conical surface (e.g., up to around 4-fold greater) than in the case of a positive cone embodiment, the alignment of the axes of the protective cap 315 and the conical surface 320 is more precise. The negative conical surface is dimensioned to receive light from an open end of the tube 315 through the curved surface 343 and reflect this light radially to form the output 330. The alignment precision during fusion affects the symmetry of the optical element within the inner surface of the tube and the fact that light reflected from the negative conical surface 345, entering the cap 315 does not traverse a refractive index change eliminates Fresnel reflections that occur in positive cone embodiments. FIG. 17B is included for comparison of the ray tracing of the output to FIG. 16B (both assume operation in air) and FIG. 17C is offered for comparing the output 340 in saline or blood to that in air 330 where all other variables are held substantially constant.

In a related implementation, the convex surface 343 of the embodiment of FIG. 17 can be replaced with a concave surface 350 (in the embodiment shown in FIG. 18), thereby changing the optical power of the corresponding optical element 388 traversing the axis of the cap 355. In the example of FIG. 18, some additional angular redirection of light may be accomplished, as shown by 375, when the embodiment is operated in whole blood, to achieve light divergence similar to that in the embodiment utilizing a positive conical surface. The optical element 388 bound by a cylindrical outer surface and the concave surface 350 and a negative conical surface 360 along the axis is quite short, 383, and borders on the limits of manufacturability, but the overall diameter of the resulting device is similar to that of other embodiments. The conical surface 360 is dimensioned to receive light through the open end of the tube 355 and through the curved surface 350 and reflect this light internally to the optical element 388 and radially away from the axis of the tube 355. The optical element 388 may be fused, 370, within the bore of the protective cap 355 and annealed. When the cap 355 is cooperated with an optical fiber element inserted therein, preferably the tapered fiber element 365 abuts the concave surface 350 of the optical element 388 at the cladding of the taper such that an air gap remains between the core of the tapered end 380 and the concave surface 350. Some residual axially-directed emission 385 may remain with the use of use embodiment due to the non-zero area of the rounding of the apex 362 of the negative conical surface 360.

Imperfections of conical apices are a common cause leading to axially-directed emission. Here, the axial emissions can be eliminated by preventing light from reaching a conical apex. In one example, as provided in FIG. 19, the optical element 400 can include a right circular frustum 410 rather than a complete cone with apex (i.e., a conical surface of such cone is a frustoconical surface); in another example the cone retains or includes a rounded apex. Additionally and in this example, the optical element 400 includes a convex lens surface 430 and the optical element is fused, 435, to the tube 420. In this embodiment, the apex geometry is less important because the laser delivery fiber(s) includes an annular fiber termination 405 (e.g., via a solid to annular conversion, an annular fiber coupled to the laser source, or an annular (ring) bundle of several fibers).

As shown in the ray trace in FIG. 19B, the use of fiber 405 with an annular cross-section removes the conical apex or frustum face from the optical path, and all light rays from the annular fiber or annular bundle 405 impinge on the surface 440 configured to provide for TIR and distal from the apex or the frustum face. In this instance, light divergence remains low and the output has true orthogonal character (with respect to the axis of the fiber 405). Scattering due to reflections at the conical frustum surface 440 and at the inner wall of the cap 420 may remain, but are far less problematic because these reflections ultimately exit within or very near to the desired output profile, where the output is orthogonal or near orthogonal.

In yet another related embodiment, apical irregularities in radial emission systems can be substantially eliminated by employing a melt-collapsed optical element. Here, the negative apex of the optical element can be formed from melt collapsing a tube rather than machining as depicted in FIG. 20. Such apices can be produced with very small dimensions, for example, the apex dimensions can be smaller than or less than the wavelength of the laser light used. Where the conical surface 460 having a more acute apex angle θ is lower angle than the (apex) angle α of the conical surface 475 forming a TIR of light internally to the optical element 480, and is lower than the maximum angle of propagation for the light within the delivery fiber 455, the result is promotion of all light modes that interact with the surface 460 to angles that are twice as large as they were prior to such interaction. This may be exploited in smoothing semi-Gaussian spatial profiles of the output distribution of light to profiles with more top-hat character, but requiring a reduction in the maximum reflecting cone 475 angle α for TIR at the same time, thereby typically reducing the potential for designing an orthogonally-directed light output.

Notably, two structures can be produced from melt-collapsed conical apices: higher angle TIR surfaces that redirect incident rays outside the fiber device, and lower angle surfaces that redirect apical rays toward a radial position, preferably toward a second reflective surface. Preferably, the herein described optical element includes a melt collapsed conical apex with a low apex angle (2θ) and a machined TIR surface that has an apex angle (2α) as provided in the above embodiments. Herein, the melt-produced or collapsed cone angle (2θ) is, preferably, substantially smaller than the fiber initial internal divergence angle and/or less than, approximately, the arcsine of the numerical aperture divided by the refractive index of the glass assuming the gas or vacuum within the sealed space 478 has a refractive index of approximately 1. That is, the optical element 480, for example as shown in FIG. 20, can include an up-tapered negative cone. As used herein, the up-tapered negative cone includes two conical surfaces which are distinguished by different cone angles or apex angles. By way of distinction, the up-tapered negative cone includes a melt collapsed conical apex 465 that has an up-tapered apex angle (2(0) that is less than about 10°, preferably less than 9°, 8°, 7", 6°, or 5". The up-tapered negative cone further includes a TIR cone that has a TIR apex angle (2α), notably the precise apical point of the TIR cone is within the negative space of the up-tapered negative cone. The TIR apex angle is in a range of about 70° to about 115°, about 70° to about 110°, about 70° to about 105°, about 70 to about 104°, about 70 to about 100°, about 75° to about 104°, about 75° to about 100°, about 80° to about 104°, about 80° to about 100°, about 85° to about 104°, or about 85° to about 100°.

As shown in FIG. 20A, the optical fiber termination can prevent axial emission by employing an up-tapered conical solid to annular beam converter 460. The optical element 480, preferably, includes an apical point 465 that has a smaller diameter than a wavelength of surgical light, for example, the apical point, preferably, has a diameter of less than 800 nm, 750 nm, 700 nm, 650 nm, 600 nm, 550 nm, 500 nm, 400 nm, 350 nm, 300 nm, or 250 nm. The optical element 480 further includes a TIR conical surface 475, for example machined into a melt collapsed tube pursuant to the description provided in reference to FIG. 17. The optical element 480, preferably made at least in part from fused quartz or fused silica, and having an input face 470 proximal to the open end of the glass tube 490 and the conical faces 460 & 475 proximal to the closed end of the glass tube 490. The input face 470 can include a flat face, a convex lens, a concave lens, an annular lens, or a combination thereof. Preferably, the input face 470 is a convex lens. Herein, the optical element 480 is fused 485 to the tube 490 yielding a one-piece unitary construction that, preferably, is made at least in part from fused quartz or fused silica.

The radial emission optical fiber termination can further include a silica core fiber 455. The silica core fiber 455 carries a polymer (e.g., nylon) jacket or coating and, preferably, the polymer jacket or coating is affixed to (e.g., adhesively) the internal surface of the glass tube 490. In one instance, the silica core fiber 455 includes an up-tapered terminus.

In FIG. 20B the radial emission 495 displays similar divergence to the delivery fiber 455 and has orthogonal character. Scatter is greatly reduced due to the fusion 485 of the cylindrical optical element 480 within the cap 490 and any scatter that remains due to imperfections in the fusion region 485 largely overlaps the intended output. Notably in this embodiment, this embodiment eliminates axial emissions and redirects all incident light as axial emissions.

Figure 21:
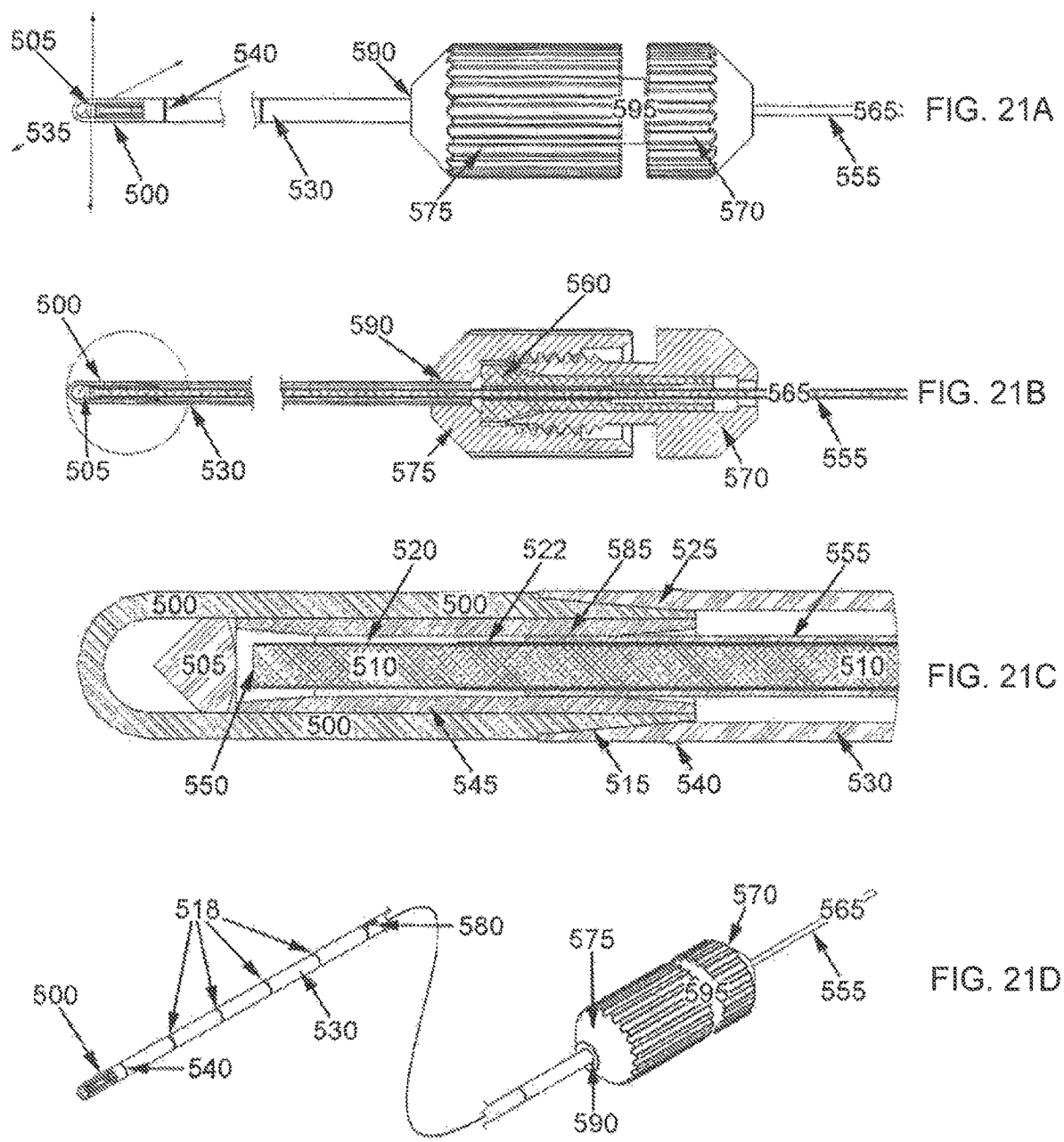
FIG. 21 includes sub-FIGS. 21A, 21B, 21C, and 21D.

FIG. 21 (with sub-FIGS. 21A, 21B, 21C, and 21D) depicts a resposable embodiment of the invention, where "resposable" means a device within which a component or components, such as a surgical tip or patient contact assembly, is optionally disposable and in which one or more other components, such as a transmitting fiber optic conduit for use with the optionally disposable part, is reusable. A transmitting optical fiber 565, herein a polyamide or poly-amide-imide (e.g. nylon) buffered 555, fluoropolymer coated 522, fluorine-doped silica clad 520 and silica core optical fiber 510, has a prepared output tip 550 that is protected by a centering sleeve 545 made of glass, ceramic or metal, disposed about the fiber outer diameter and attached 585 with adhesive or crimping to the fiber buffer 555. Other mechanisms for protecting the transmitting fiber tip 550 will be apparent to those skilled in the art. Preferably, the fiber and centering sleeve are not attached to the fiber cap 500 containing the radial emission optical element 505. In one instance, the fiber cap is chamfered 515 to mate with a matching chamfer 525 within a cannula 530, preferably a semi-rigid cannula. In another instance, the fiber cap 500 is hermetically attached (e.g., adhesively) to the cannula 530.

The semi-rigid cannula 530 can be attached 590 by means of adhesive, solvent welding or other method to a cannula-mount segment 575 of a fiber control device (e.g., a pin vise) 595 having components made of rigid polymer or metal. Accordingly, the fiber cap 500, cannula 530 and cannula-mount segment 575 form a detachable subassembly that includes the entirety of patient contacting components. Notably, the fiber control device 595 includes at least two separable components: a cannula-mount segment 575 and a fiber-holding segment 570. In one instance, the cannula-mount segment 575 and the fiber-holding segment 570 are reversibly affixed by, for example, matching screw threading. Additional reversibly means of affixing the cannula-mount segment 575 and the fiber-holding segment 570 include snap closures, pin-vise connections, a bayonet mount, a BNC-style connector, a RF connector, a UHF connector, a SMA connector, a SMB connector, a SMC connector, a TNC connector, a N connector, a C connector, or the like. The laser connector (not depicted), transmitting fiber optic conduit 565 and the fiber-holding segment 570 (which can include a fiber retaining collet 560) represent a second subassembly comprised of components that are not in patient contact and represent approximately 80% of the device cost.

As a placement aid to use in surgery, the cannula 530 is marked with clearly visible bands spaced one centimeter apart 518, where the first mark 540 is positioned one centimeter proximal to the radial output 535 indicated by the small arrows. Additional markings 580 provide a guide to the depth of insertion; in this case the marking 580 reads "5 cm". By loosening the fiber control device 595, the cap 500, cannula 530 and the cannula-mount segment 575 may be discarded and replaced intraoperatively, greatly reducing the cost of disposable material.

When definitions of terms used in this disclosure override those provided earlier in patent application Ser. Nos. 16/122,982 and/or 14/944,266 when such in conflict with those provided earlier. The invention as recited in claims appended to this disclosure is intended to be assessed in light of the disclosure as a whole, including the recitations in the claims and features disclosed in prior art to which reference is made.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

Modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s). In addition, the terminology used herein is with the purpose of describing particular embodiments only, and is not intended to limit the scope of the present invention.

The invention claimed is:

1. An article of manufacture comprising:
    an optical-fiber protective cap dimensioned to be cooperated with an optical fiber to accept light from said optical fiber and, upon propagation of said light through the optical-fiber protective cap, to output the light in a radial direction with respect to the optical fiber,
    the optical-fiber protective cap including:
    a tube having an open end and a sealed end, the tube having an axis;
    an optical element dimensioned as an optical lens element with an input curved optical surface facing the open end and an output optical surface facing the closed end; and
    a cone of an optical material that is co-axial with the axis and oriented such as to receive said light from the open end through the output optical surface and a surface of a base of the cone and to transmit said light through a conical surface of the cone away from the axis.

2. The article of manufacture according to claim 1, wherein the optical element is configured as a positive optical lens element.

3. The article of manufacture according to claim 1, wherein a circumference of said optical element is irremovably connected with an internal surface of said tube.

4. The article of manufacture according to claim 1, wherein the optical element, the sealed end, and a wall of the tube aggregately limit a portion of a volume of the hollow of the tube containing said cone.

5. The article of manufacture comprising a cannula connected to the optical-fiber protective cap of claim 1.

6. The article of manufacture according to claim 5, comprising a cannula-mount segment of a fiber-control device affixed to the cannula.

7. The article of manufacture according to claim 6, further comprising the optical fiber cooperated with the fiber control device and inserted into said optical-fiber protective cap.

8. The article of manufacture according to claim 7, further comprising a centering sleeve disposed about the optical fiber, wherein an output tip of the optical fiber is proximal to the input curved optical surface, and wherein the centering sleeve is disposed about the output tip.

9. An article of manufacture comprising:
    an optical-fiber protective cap dimensioned to be cooperated with an optical fiber to accept light from said optical fiber and, upon propagation of said light through the optical-fiber protective cap, to output the light radially with respect to the optical fiber,
    the optical-fiber protective cap including:
    a tube having an open end and a sealed end, the tube having an axis;
    an optical element having an input curved optical surface facing the open end; and
    a conical surface positioned to receive said light from the open end through the input curved optical surface and to transfer said light through said conical surface away from the axis.

10. The article of manufacture according to claim 9, wherein the conical surface is either an output surface of said optical element that limits a spatial extent of the optical element along the axis, or a surface of a cone having a base surface facing said optical element and separated from the optical element by a gap.

11. The article of manufacture according to claim 9, wherein the input curved optical surface is a convex surface.

12. The article of manufacture according to claim 9, wherein said conical surface is positioned to transfer said light through the conical surface in reflection of said light off of the conical surface.

13. The article of manufacture according to claim 9, wherein a circumference of said optical element is irremovably connected with an internal surface of said tube.

14. The article of manufacture according to claim 9, wherein the optical element, the sealed end, and a wall of the tube aggregately limit a portion of a volume of the hollow of the tube.

15. The article of manufacture comprising a cannula connected to the optical-fiber protective of claim 9.

16. The article of manufacture according to claim 15, comprising a cannula-mount segment of a fiber-control device affixed to the cannula.

17. The article of manufacture according to claim 16, further comprising the optical fiber cooperated with the fiber control device and inserted into said optical-fiber protective cap.

18. The article of manufacture according to claim 17, further comprising a centering sleeve disposed about the optical fiber, wherein an output tip of the optical fiber is proximal to the input curved optical surface, and wherein the centering sleeve is disposed about the output tip.

* * * * *